US011559684B2

(12) United States Patent
Deterre et al.

(10) Patent No.: US 11,559,684 B2
(45) Date of Patent: Jan. 24, 2023

(54) PHOTOSENSITIVE ARRAY

(71) Applicant: PIXIUM VISION SA, Saint Antoine (FR)

(72) Inventors: Martin Deterre, Paris (FR); Elodie Bouillet, Paris (FR)

(73) Assignee: Pixium Vision SA, Saint Antoine (FR)

(*) Notice: Subject to any disclaimer, the term of this patent is extended or adjusted under 35 U.S.C. 154(b) by 193 days.

(21) Appl. No.: 16/631,029

(22) PCT Filed: Jul. 13, 2018

(86) PCT No.: PCT/EP2018/069159
§ 371 (c)(1),
(2) Date: Jan. 14, 2020

(87) PCT Pub. No.: WO2019/012142
PCT Pub. Date: Jan. 17, 2019

(65) Prior Publication Data

US 2020/0147385 A1 May 14, 2020

(30) Foreign Application Priority Data

Jul. 14, 2017 (EP) .................................... 17181558

(51) Int. Cl.
*H01L 27/146* (2006.01)
*A61N 1/36* (2006.01)
*A61N 1/05* (2006.01)

(52) U.S. Cl.
CPC ....... *A61N 1/36046* (2013.01); *A61N 1/0543* (2013.01); *H01L 27/1461* (2013.01); *H01L 27/1462* (2013.01); *H01L 27/14649* (2013.01)

(58) Field of Classification Search
CPC ............. A61N 1/0543; A61N 1/36046; H01L 27/1461; H01L 27/1462; H01L 27/14649
See application file for complete search history.

(56) References Cited

U.S. PATENT DOCUMENTS

| | | | |
|---|---|---|---|
| 2,753,937 | A | 7/1956 | Bottenhorn |
| 11,171,163 | B2 | 11/2021 | Deterre |
| 2003/0097165 | A1 | 5/2003 | Krulevitch |
| 2005/0090874 | A1 | 4/2005 | Wu |
| 2005/0131490 | A1 | 6/2005 | Palanker |
| 2010/0262208 | A1 | 10/2010 | Parker |

(Continued)

FOREIGN PATENT DOCUMENTS

| | | | |
|---|---|---|---|
| CN | 1431921 | A | 7/2003 |
| CN | 101266346 | A | 9/2008 |

(Continued)

OTHER PUBLICATIONS

Lorach Henri et al, "Photovoltaic restoration of sight with high visual acuity", Nature Medicine, Apr. 27, 2015, pp. 476-482, vol. 21, No. 5. (Year: 2015).*

(Continued)

*Primary Examiner* — Kevin K Pyo
(74) *Attorney, Agent, or Firm* — Workman Nydegger

(57) ABSTRACT

The present invention relates to photosensitive arrays comprising a plurality of photosensitive elements disposed in or on a suitable substrate. The photosensitive arrays are useful as implants, in particular as retinal implants. Methods for manufacturing such arrays are also provided.

41 Claims, 13 Drawing Sheets

(56) References Cited

U.S. PATENT DOCUMENTS

| | | | |
|---|---|---|---|
| 2012/0032595 | A1 | 2/2012 | Shim |
| 2012/0109292 | A1 | 5/2012 | Barbosa |
| 2012/0109296 | A1 | 5/2012 | Fan |
| 2012/0153423 | A1 | 6/2012 | Lee |
| 2014/0111088 | A1 | 4/2014 | Shim |
| 2017/0070180 | A1 | 3/2017 | Mills |
| 2018/0064929 | A1 | 3/2018 | Deterre |
| 2018/0182788 | A1 | 6/2018 | Deterre |
| 2019/0009075 | A1 | 1/2019 | Deterre |
| 2020/0251507 | A1 | 8/2020 | Deterre |

FOREIGN PATENT DOCUMENTS

| | | | |
|---|---|---|---|
| CN | 101317128 | A | 12/2008 |
| CN | 101330090 | A | 12/2008 |
| CN | 101483091 | A | 7/2009 |
| CN | 102222450 | A | 10/2011 |
| CN | 103260560 | A | 8/2013 |
| CN | 103681701 | A | 3/2014 |
| CN | 104022130 | A | 9/2014 |
| CN | 104873330 | | 6/2017 |
| EP | 3144032 | | 3/2017 |
| JP | 62-172765 | A | 7/1987 |
| JP | 2006-054252 | A | 2/2006 |
| JP | 2006-517435 | A | 7/2006 |
| JP | 2012-506623 | A | 3/2012 |
| JP | 2014-503229 | | 2/2014 |
| JP | 2014-503229 | A | 2/2014 |
| KR | 10-1234214 | B1 | 2/2013 |
| WO | 2004/067088 | A1 | 8/2004 |
| WO | 2008/050726 | A1 | 5/2008 |
| WO | 2010/048291 | A1 | 4/2010 |
| WO | 2012058477 | | 5/2012 |
| WO | 2013/142815 | A1 | 9/2013 |
| WO | 2016180517 | | 11/2016 |
| WO | 2016180535 | | 11/2016 |

OTHER PUBLICATIONS

Wang L., et al.; "Photovoltaic retinal prosthesis: implant fabrication and performance; Photovoltaic retinal prosthesis: implant fabrication and performance" Journal of Neural Engineering; Institute of Physics Publishing; Bristol, GB; vol. 9, No. 4; Jul. 12, 2012; p. 46014.

Boinagrov David et al, "Photovoltaic Pixels for Neural Stimulation: Circuit Models and Performance", IEEE Transactions on biomedical circuits and systems, IEEE, Feb. 2016, pp. 85-97, vol. 10, No. 1, US.

International Search Report and Written Opinion for PCT/EP2016/000690 dated Jul. 29, 2016.

International Search Report and Written Opinion for PCT/EP2016/000776 dated Aug. 22, 2016.

International Search Report and Written Opinion for PCT/EP2016/001073 dated Sep. 5, 2016.

International Search Report and Written Opinion for PCT/EP2016/001545 dated Jan. 3, 2017.

Loudin et al., "Photodiode Circuits for Retinal Prostheses", IEEE transactions on biomedical circuits and systems, vol. 5, No. 5, Oct. 2011, pp. 468-480.

Mandel et al., "Cortical responses elicited by photovoltaic subretinal prostheses exhibit similarities to visually evoked potentials", Nature Communications, 4:1980, DOI: 10.1038/ncomms2980, received Oct. 20, 2012, pp. 1-9.

Dae Yeong Lee, et al., "Implantation of Modular Photovoltaic Subretinal Prosthesis", Ophthalmic Surgery, Lasers & Imaging Retina, Feb. 2016, vol. 47, No. 2, pp. 171-174.

* cited by examiner

A

B

PHOTOSENSITIVE ARRAY

The present invention relates to a photosensitive array comprising photosensitive elements disposed in or on a substrate, which may further optionally be coated, and a method for manufacturing the same.

There exists a variety of different diseases of the retina that are caused by a degeneration of the photosensitive cells of the retina. Examples of degenerative diseases include age-related macular disease (AMD) and retinitis pigmentosa (RP), which are major causes of blindness, especially among the elderly worldwide. Both diseases are degenerative and associated with a loss of the photoreceptive cells (photoreceptors) of the retina. AMD causes loss of central vision, while RP initially causes gradual loss of peripheral vision, followed by loss of central vision resulting in complete blindness.

The retina is a light-sensitive layer at the back of the eye that includes almost one hundred thousand photoreceptor cells called rods and cones, which have the task of converting the energy from incident light into a nerve signal that is transmitted via the optic nerve to the visual cortex of the brain. Degeneration of the photoreceptor cells in AMD and RP progressively renders the retina less sensitive to light, and ultimately causes loss of sight. Importantly, the neural cells of the retina and the optic nerve are not affected as severely by the disease as the photoreceptor cells. Hence, there is still an intact and viable connection between the retina and the brain, which can be exploited for restoring vision.

Visual prosthesis systems comprising a retina implant have been developed which are helpful tools for at least partially re-establishing a modest visual perception and a sense of orientation for blind and visually impaired users by exploiting the fact that, although parts of the retinal tissue have degenerated, most of the retina may remain intact and may still be stimulated directly by light dependent electrical stimuli. Typically, retinal implants are implanted into the patient's eye, effecting electrical excitation of the remaining neuronal cells upon light stimulation. When being stimulated, these remaining neuronal cells convey the artificially induced electrical impulses to the visual part of the brain through the optic nerve.

Retinal implants can be broadly divided into two categories: epi- and sub-retinal (Lin et al., 2015, Retinal prostheses in degenerative retinal diseases, J Chin Med Assoc.; 78(9): 501-5). Epi-retinal devices are placed on or near the inner surface of the retina, i.e. the side of the retina which is first exposed to incident light and along which the nerve fibers of the ganglion cells pass on their way to the optic nerve. Epi-retinal implants typically comprise a chip with a plurality of pixels capable of receiving an image projected by an extraocular device (typically a camera and a microelectronic circuit for decoding incident light) onto the retina through the lens of the eye, for converting the image into electrical signals and for further conveying the signals into electrical stimuli via a plurality of stimulation electrodes to stimulate the retinal cells adjacent the chip, in order to reconstruct or improve vision of blind or partially blind patients. In contrast, sub-retinal devices are placed under the retina, between the retina and the underlying retinal pigment epithelium or other deeper tissues Currently available retinal implant technologies rely on the implantation of a single chip. WO 2016/180535 A1, EP 3 144 032 A1 and Wang et al. J Neural Eng. 2012 August; 9(4):046014 describe rigid and planar chips (photosensitive elements), each comprising a plurality of pixels arranged in an array. US 2003/0097165 A1, US 2005/0090874 A1 and WO 2012/058477 A2 provide more flexible chips (photosensitive elements). All of the aforementioned prior art documents are typical examples for commonplace approaches in the field of retinal implants, which rely on the implantation of one single photosensitive chip or element. These approaches, however, come with certain drawbacks, in particular in terms of handling during implantation (which may result in damage to the chip or the surrounding tissue), and a limited field of vision. Furthermore, the prior art implants, once inserted, easily shift out of place (which results in impaired vision), and are prone to corrosion from contact with environmental liquids (which damages the implant).

It would thus be desirable to provide a solution that overcomes the drawbacks associated with the prior art technology and enhance both the handling of the chip during surgery as well as the therapeutic benefit for the patient.

Although the present invention is described in detail below, it is to be understood that this invention is not limited to the particular methodologies, protocols and reagents described herein as these may vary. It is also to be understood that the terminology used herein is not intended to limit the scope of the present invention which will be limited only by the appended claims. Unless defined otherwise, all technical and scientific terms used herein have the same meanings as commonly understood by one of ordinary skill in the art.

In the following, the elements of the present invention will be described. These elements are listed with specific embodiments, however, it should be understood that they may be combined in any manner and in any number to create additional embodiments. The variously described examples and preferred embodiments should not be construed to limit the present invention to only the explicitly described embodiments. This description should be understood to support and encompass embodiments which combine the explicitly described embodiments with any number of the disclosed and/or preferred elements. Furthermore, any permutations and combinations of all described elements in this application should be considered disclosed by the description of the present application unless the context indicates otherwise.

Throughout this specification and the claims which follow, unless the context requires otherwise, the term "comprise", and variations such as "comprises" and "comprising", will be understood to imply the inclusion of a stated member, integer or step but not the exclusion of any other non-stated member, integer or step. The term "consist of" is a particular embodiment of the term "comprise", wherein any other non-stated member, integer or step is excluded. In the context of the present invention, the term "comprise" encompasses the term "consist of". The term "comprising" thus encompasses "including" as well as "consisting" e.g., a composition "comprising" X may consist exclusively of X or may include something additional e.g., X+Y.

The terms "a" and "an" and "the" and similar reference used in the context of describing the invention (especially in the context of the claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. No language in the specification should be construed as indicating any non-claimed element essential to the practice of the invention.

The word "substantially" does not exclude "completely" e.g., a composition which is "substantially free" from Y may be completely free from Y. Where necessary, the word "substantially" may be omitted from the definition of the invention.

The term "about" in relation to a numerical value x means x±10%.

All values provided herein with respect to absolute or relative relations of parameters or regarding the values of parameters themselves are subject to statistical error and/or to design constraints and variations. Accordingly, values provided should be considered to be representative of values ranging at least +/−25% about that value provided or at least +/−10 μm, where it is referred to sizes. For instance, a three-diode pixel with a size of 100 μm, allows optimal values for the electrode size in a range of approximately from 15 μm to 30 μm.

In the present invention, if not otherwise indicated, different features of alternatives and embodiments may be combined with each other.

Photosensitive elements (chips) were developed as implants for visual restoration in patients suffering from a degeneration of the outer retina such as AMD (dry Age-related Macular Degeneration) or RP (Retinitis Pigmentosa). In order to optimize function, handling and therapeutic benefit, the present inventors developed the idea to provide an array of at least one electrically stimulating, preferably photosensitive element, preferably several electrically stimulating, preferably photosensitive elements, supported by or embedded within a suitable substrate. According to special embodiment where several photosensitive elements are implanted, the provision of substrates may ensure the required arrangement and distance of the implanted chips. Further, suitable substrates preferably facilitate handling during surgery (including implantation and explantation for implant removal or change). Encapsulation of the photosensitive element in a suitable soft biocompatible material (either as substrate or as an additional coating) preferably protects the implant from damage during implantation. Moreover, encapsulation may advantageously improve post-implantation healing by reducing the mechanical trauma caused by the rigid, planar chips during or after surgery.

In a first aspect, the present invention provides an electrically stimulating array comprising at least one stimulating element, preferably at least two stimulating elements, said stimulating elements each comprising at least one stimulating electrode, wherein said stimulating element is disposed in or on a substrate. Optionally, the said stimulating element further comprises a counter electrode and/or a resistor.

In preferred aspect, the present invention provides a photosensitive electrically stimulating array (the "photosensitive array") comprising at least one photosensitive element, preferably at least two photosensitive elements, said photosensitive elements each comprising at least one pixel having at least one diode and a stimulating electrode, wherein said photosensitive element is disposed in or on a substrate as described herein. Optionally, said pixel further comprises a counter electrode and/or a resistor. When present, the resistance of the resistor may preferably be chosen according to a predetermined relation of resistance, size of the stimulating electrode, and size of the diode. The photosensitive array may optionally further comprise a coating.

Photosensitive Array

A "photosensitive array" according to the invention comprises or consists of an array of at least one photosensitive element ("chip"), preferably at least two photosensitive elements, disposed in or on a substrate. Put differently, an "array" or "photosensitive array" according to the invention is preferably characterized by the presence of at least two photosensitive elements (chips) disposed in or on a substrate. Each photosensitive element (chip) comprises at least one pixel, or preferably a plurality of pixels which are arranged in (pixel) arrays on or in the photosensitive element.

The inventive arrays may thus also be referred to as "substrate-supported arrays" or "embedded arrays" herein, depending on whether the substrate is configured as a supporting layer or a capsule. The preferred use of a plurality of photosensitive elements allows to cover a large visual field when implanted into an eye and may additionally facilitate handling of the array during implantation and/or explantation into a body part of interest (e.g. an eye). The inventive arrays may further comprise a coating which may preferably protect both the photosensitive elements and the surrounding cells/tissues from damage, and/or improve further properties of the substrate-supported or embedded array as described elsewhere herein.

Generally, any type of electrically stimulating element, preferably any type of photosensitive element, applicable as an implant in the target region of interest (e.g. a retinal implant) can be provided in the form of an electrically stimulating, preferably photosensitive, array of the invention. For instance, retinal implants are currently typically provided in the form of rigid, planar chips, which are individually delivered to the patient's eye where they contact the retina. Preferably, the photosensitive elements of the inventive array may be characterized by the features and parameters described elsewhere herein (and further as "implants" in in WO 2016/180517 A1, WO 2016/206809 A1, WO 2017/045756 A1). However, as indicated previously, other types of electrically stimulating or in particular photosensitive elements may be arranged in or on a substrate, and optionally coated, as described herein, as well—thereby forming an electrically stimulating, preferably photosensitive, array according to the present invention.

Substrate

The inventive electrically stimulating, preferably photosensitive, arrays described herein comprise a suitable substrate (and optionally further a coating).

The substrate can be configured in different ways. In some arrays according to the invention, the substrate may be configured as a supporting layer, whereon the electrically stimulating, preferably photosensitive elements are disposed. Such arrays are also referred to as "(substrate-) supported" arrays herein. In other arrays according to the invention, the substrate may be configured as a capsule, wherein the photosensitive elements are disposed. Such arrays are also referred to as "embedded" arrays herein. In some arrays, the two different types of substrates are combined. Such arrays are also referred to as "combined" arrays herein. Irrespective of the specific configuration of the substrate, the inventive array may further comprise a coating contacting or surrounding the array.

Generally, the unprecedented use of a substrate to support and/or encapsule electrically stimulating, preferably photosensitive, elements as described herein preferably comes with several advantages. It may preferably facilitate manufacturing and/or handling of the electrically stimulating, preferably photosensitive, elements and the inventive arrays. In addition, the substrate may preferably enhance therapeutic effect and patient's compliance.

Particular advantages of the inventive arrays comprising a substrate may include one or more of the following:

- Facilitates delivery of a plurality of electrically stimulating, preferably photosensitive, elements as described herein
- Conforms better to non-planar/curved/irregular shapes (such as the shape of the eye) as compared to flat chips implanted individually
- Optimizes benefits/functionality of the electrically stimulating, preferably photosensitive, elements by tiling to deliver more pixels
- Facilitates handling of the electrically stimulating, preferably photosensitive, elements and avoids damage to said elements
- Eases contact with body structures or tissues and avoids trauma
- Can be used for drug delivery and complementary therapy
- Enables distinction of arrays' front and back side, thereby facilitating manufacturing and handling, inter alia during implantation
- Enables arrangement of electrically stimulating, preferably photosensitive, elements in a desired pattern for optimized therapeutic results and/or particular areas of application.

The substrate (and inventive array) is preferably flexible enough to conform to the shape of the site of implantation (e.g. the (human) eye). Thus, the substrate may for instance be flexible enough to be bent to a radius of curvature close to about 12 mm, about the average radius curvature of a human retina.

As the substrate (and inventive array) is preferably bendable to conform to the curvature of a retina, the neuron-to-electrode distance between electrodes of the device and target neuron cells of the retina can be reduced. Consequently, the power required in each pixel to excite or stimulate the neuron cells may be reduced to enable a higher pixel density with the allowed power density given and improve resolution of images perceived via the neuron cells.

Further, the substrate (and inventive array) is preferably rigid enough to provide sufficient support to the electrically stimulating, preferably photosensitive, elements and optionally after implantation. Thus, the substrate is preferably rigid enough to preferably prevent folding of the array and stacking of the electrically stimulating, preferably photosensitive, elements.

Further considerations that may be taken into account include the translucency of the inventive array. For example, it may be desirable to provide an array that is thin enough to allow passing through of a certain portion of light.

The thickness of the substrate is preferably chosen to meet any or all of the above requirements. Preferably, the thickness of the substrate may be between 1 μm and 500 μm, more preferably between 10 μm and 200 μm, most preferably between 10 μm and 100 μm. Specifically, the substrate may have a thickness of at least 10 μm, 20 μm, 30 μm, 40 μm, 50 μm, 60 μm, 70 μm, 80 μm, 90 μm, 100 μm or 150 μm.

The inventive arrays may, in addition to the substrate upon or wherein which the at least one electrically stimulating, preferably photosensitive, elements are disposed, further comprise a coating contacting and optionally surrounding said elements supported by or embedded within the substrate material. Many considerations applying to the substrate of the inventive array apply to the coating as well. In the following, reference is thus made to the "substrate (and/or optionally coating) material" or "substrate (and/or coating)".

The substrate (and/or optional coating) material may preferably be biocompatible, i.e. compatible with living tissue/cells or a living system by not being toxic, injurious, or physiologically reactive and not causing immunological rejection. The substrate (and/or optional coating) material may be, at least partially, biodegradable, i.e. capable of being broken down into smaller pieces and/or its components (especially into innocuous products) after implantation, i.e. under physiological conditions (e.g. by the action of cells, bodily fluids, etc.). Biodegradable substrate (and/or optionally coating) materials may be degraded within minutes to hours ("fast biodegradable substrates/coatings") after implantation or within days to weeks ("slowly biodegradable substrate/coating materials") after implantation of the inventive array.

In order to ensure targeted electrical stimulation, the substrate (and/or optional coating) material may preferably be (essentially) electrically non-conductive, i.e. essentially unable to conduct an electric current. In this context, "essentially" means that minimal electric currents may be conducted, however, as long as they do not interfere with the appropriate function of the electrically stimulating array, preferably photosensitive array. Alternatively, the substrate (and/or optionally coating) material may preferably be electrically conductive, i.e. able to conduct an electric current, and optionally is connected to at least one ground electrode.

The substrate (and/or optional coating) may be opaque, translucent or transparent. Specifically, the top and bottom side of the substrate (and/or optionally coating) may be colored, optionally colored differently. Different coloring may advantageously allow differentiation of the bottom and top (also referred to as "front" and "back") sides of the substrate (and/or optional coating) and thus proper orientation of the array during implantation into the body part of interest (e.g. the human eye). A distinctive coloration may thus facilitate correct handling and implantation. However, the substrate (and/or optional coating) may also be non-colored/transparent.

The inventive array of electrically stimulating, preferably photosensitive, element is particularly envisaged for implantation into the (human) body where the stimulating electrodes preferably stimulate target cells or tissues. Thus, the substrate (and/or optionally coating) may preferably be configured to enable the stimulating electrodes of the electrically stimulating, preferably photosensitive, elements to electrically stimulate target cells/tissues. To that end, the substrate (and/or optional coating) may preferably enable an electrical current to be transferred from the stimulating electrodes to the target cells/tissues. Specifically, and in particular when electrically non-conductive materials are used as substrate (and/or optional coating) materials and cover the stimulating electrodes of the inventive array, the substrate (and/or the optional coating) may comprise notches or holes where it contacts and optionally covers the stimulating electrodes of the electrically stimulating, preferably photosensitive, elements. However, notches and holes may be present anywhere in the substrate (and/or the optional coating), e.g. to facilitate the flow of gases or fluids.

Suitable substrate (and optional coating) materials are exemplified in the context of supported, embedded and coated arrays below.

The substrate (and/or optional coating) of the inventive array may further comprise therapeutic agents. The term "therapeutic agent" as used herein includes an active force, entity or substance capable of producing a therapeutic effect. Therefore, the term includes drugs (including small organic molecules, and biologicals such as peptides, proteins, antibodies), cells and nucleic acids (including single and double strand RNA and DNA in "free" form, or provided in the form of suitable vectors).

Therapeutic agents of particular interest include anti-infective agents, anti-inflammatory agents, therapeutic cells, and gene therapy vectors.

Anti-infective agents include any agent capable of acting against infection, either by inhibiting the spread (i.e. propagation and/or growth) of an infectious agent or by killing the infectious agent itself. Infectious agents include bacteria, viruses, infectious proteins, fungi, parasites or protozoals. Suitable anti-infective agents in the context of the present invention include antibiotics, antiprotozoals, anthelmintics, antifungals, antimalarials, antituberculotics, antileprotics, aminoglycosides, penicillins, cephalosporins, tetracyclines, sulfonamides, fluoroquinolones, antivirals, macrolides or combinations thereof.

Anti-inflammatory agents include any agent capable of reducing or preventing inflammation. Suitable anti-inflammatory agents in the context of the present invention include non-steroidal anti-inflammatory drugs (NSAIDs), immune selective anti-inflammatory derivatives (ImSAIDs), anti-inflammatory bioactive compounds, steroids including cortico- and glucocorticoids or anti-VEGF.

When using the electrically stimulating array, preferably photosensitive array of the invention as a retinal implant, therapeutic cells of interest particularly include cells capable of restoring or replacing degraded retinal cells or cells capable of maintaining surviving retinal cells and/or preventing their loss. For instance, retinal pigment epithelium (RPE) cells have important functions in the maintenance of homeostasis of the outer retina. These functions include regulating the transport of nutrients to the photoreceptors, phagocytosing shed outer segments, and absorbing stray light. The present invention therefore envisages use of RPE cells as therapeutic agents in the substrate and/or coating of the inventive array. RPE cells may be derived from the periphery of the patient's retina or from induced pluripotent stem cells (iPSCs) generated from patient's cells (e.g. fibroblasts) (autologous transplantation) or may be derived from human embryonic stem-cells (hESC-RPE) or umbilical cord blood-derived stem cells.

About 70 percent of people with the X-linked form of RP carry mutations that cause loss of function of the retinitis pigmentosa GTPase Regulator (RPGR) gene, which encodes a protein important for maintaining the health of photoreceptors. To overcome the effects of genetic mutations causing disease (e.g. EP), gene therapy agents can be used as therapeutic agents in accordance with the invention. Gene therapy agents include suitable vectors delivering non-mutated forms of genes into the target cell to induce or restore expression of the desired (functional) gene product. Vectors include plasmids and viral vectors, in particular adeno-viral vectors, lentiviral vectors and Herpes simplex virus vectors. Optionally, further gene editing tools may be co-delivered as further therapeutic agents with the functional copy of the targeted gene (for instance the RPGR) gene to the retina of affected individuals. Such gene editing tools include inter alia components of the CRISPR/Cas system.

The substrate may further comprise points, barbs, hooks, and/or tacks to attach the array to the target tissue, in particular retinal tissue, and/or handles to facilitate handling during surgery.

Supported Arrays

Substrate

In "supported" arrays according to the invention, the electrically stimulating, preferably photosensitive, elements are preferably disposed on a suitable substrate that is configured as a supporting layer, in particular a film or membrane.

As explained above, suitable substrates are preferably flexible and have the ability to conform to the shape of the retina, while at the same time providing sufficient support for the electrically stimulating, preferably photosensitive, elements disposed thereon. Further, the substrate materials may preferably be biocompatible and/or electrically non-conductive.

In this regard, preferred substrate materials for supported arrays may be selected from parylene, polyimide, polydimethylsiloxane (PDMS), polyester or a polymer including poly(lactic acid) (PLA), poly(glycolic acid) (PGA), poly (lactid-co-glycolic acid) (PLGA) or a bioadhesive.

Supported arrays may have an elongated shape, e.g. the form of a strip, whereupon the electrically stimulating, preferably photosensitive, elements may be disposed in an elongated arrangement, e.g. a row or an elongated serpentine, or displaced relatively to each in an elongated arrangement.

To that end, substrates may preferably have a length of at least 1 mm, 2 mm, 3 mm, 4 mm, 5 mm, 6 mm, 7 mm, 8 mm, 9 mm or 10 mm, preferably between 3 mm and 7 mm. Substrates may preferably have a width of at least 0.1 mm, 0.2 mm, 0.3 mm, 0.4 mm, 0.5 mm, 0.6 mm, 0.7 mm, 0.8 mm, 0.9 mm, 1.0 mm, 1.1 mm, 1.2 mm, 1.3 mm, 1.4 mm or 1.5 mm, preferably between 0.5 mm to 1 mm. However, other shapes, dimensions and arrangements of electrically stimulating, preferably photosensitive, elements are also envisaged herein.

Supported arrays may further comprise a top layer comprising or consisting of a material as exemplified in the context of supporting substrate layers herein. Said typically non-biodegradable materials may preferably comprise notches or holes that allow the electric current generated in the stimulating electrode to pass to the target cells/tissues. The notches or holes may be uncovered or may be covered by a (biodegradable) coating as exemplified below. Accordingly, the electrically stimulating, preferably photosensitive, elements may be "sandwiched" between the top layer and the supporting substrate.

Coating

Electrically stimulating, preferably photosensitive, arrays of the invention, and in particular supported arrays as described herein may further be coated with a suitable coating material. Said coating material may confer additional functionalities or advantageous properties to the array. E.g., coating materials may be provided with therapeutic agents or cells. Soft, viscous and flexible coatings may further protect the brittle electrically stimulating, preferably photosensitive, elements from damage, and avoid mechanical stress or trauma for the delicate target cells/tissues during or after implantation. The coating may be contiguous (i.e. cover/surround the supported array entirely) or non-contiguous (i.e. cover only parts of the supported array). The coating may preferably be biocompatible and biodegradable. The coating may preferably be electrically non-conductive. The coating may comprise notches or holes allowing the electrical current to pass from the stimulating electrodes to the target cells/tissue. The coating may, optionally independently from the substrate, be opaque, translucent or transparent. It may be colored, wherein its upper and lower surface may be colored differently.

Specifically, useful coatings may comprise or consist of the materials exemplified as "capsule" materials below. Accordingly, suitable coating materials may be selected from collagen, hyaluronic acid, polyethylenglykol (PEG), poly(lactic acid) (PLA), poly(glycolic acid) (PGA), poly (lactid-co-glycolic acid) (PLGA), gelatin, hydrogel, or a bioadhesive.

The invention also envisages a combination of supported and embedded electrically stimulating, preferably photosensitive, elements as described herein (referred to as "combined" arrays herein). Therein, the electrically stimulating, preferably photosensitive, elements are typically disposed on a substrate configured as a supporting layer, which is embedded in a capsule as described below. Such arrays preferably combine the advantageous properties conferred by both configurations. The combined arrays may further comprise a coating as described herein.

Embedded Arrays

Substrate

In "embedded" arrays according to the invention, the electrically stimulating, preferably photosensitive, elements, are preferably disposed in a suitable substrate that is configured as capsule surrounding said photosensitive elements.

The term "capsule" refers to an enclosing structure surrounding the electrically stimulating, preferably photosensitive, elements, of the inventive array. The "capsule" may contiguously cover all sides of the (embedded) electrically stimulating, preferably photosensitive, elements, although it may comprise notches or holes. Alternatively, the "capsule" may cover only the top or bottom side of the electrically stimulating, preferably photosensitive, elements. The "capsule" may be homogenous (e.g. consist of one substrate material surrounding the electrically stimulating, preferably photosensitive, elements) or may be assembled (e.g. consist of different substrate materials, for instance comprise a top side consisting of one substrate material, and a bottom side consisting of another substrate material).

As explained above, suitable substrates may preferably be flexible and have the ability to conform to the shape of the human eye, while at the same time providing sufficient support for the electrically stimulating, preferably photosensitive, elements disposed therein. Further, the substrate should preferably be biocompatible and/or electrically non-conductive. Substrates of the "capsule-type" may—just like the coatings described herein—be biodegradable. Moreover, capsule-type substrates (and/or coatings) may be gel-like, viscous or solid.

In this regard, suitable substrate materials for embedded arrays include collagen, hyaluronic acid, polyethylenglycol (PEG), poly(lactic acid) (PLA), poly(glycolic acid) (PGA), poly(lactid-co-glycolic acid) (PLGA), gelatin, or hydrogel or a biological adhesive. As described above, these materials may be assembled to form the substrate capsule surrounding (part of) the embedded array. In case of such assembled capsules, the choice of suitable substrate materials depends on the overall assembly of the array and its intended use. It may be desired to embed the array in a capsule assembled from a biodegradable material at one side (e.g. the side, which contacts the target cells/tissues in order to maximize electrical stimulation) and a non-biodegradable material at the opposite side (e.g. the side, which does not contact target cells/tissues). Alternatively, the capsule may be assembled from a fast biodegradable material at the electrode side and a slowly biodegradable material at the nonelectrode side of the electrically stimulating, preferably photosensitive, elements.

Embedded arrays may have an elongated shape, wherein the electrically stimulating, preferably photosensitive, elements may be disposed in an elongated arrangement, e.g. a row or an elongated serpentine, or displaced relatively to each in an elongated arrangement.

To that end, substrates may preferably have a length of at least 1 mm, 2 mm, 3 mm, 4 mm, 5 mm, 6 mm, 7 mm, 8 mm, 9 mm or 10 mm, preferably between 3 mm and 7 mm, more preferably between 5 to 6 mm. Substrates may preferably have a width of at least 0.5 mm, 1.0 mm, 1.5 mm, 2.0 mm, 2.5 mm, 3 mm, 3.5 mm or 4.5 mm or preferably between 1 mm to 3 mm. However, other shapes, dimensions and arrangements of electrically stimulating, preferably photosensitive, elements are also envisaged herein.

Coating

Just like supported arrays, embedded arrays may further be coated with a suitable coating material. Suitable coating materials include the materials exemplified as "capsule" materials herein. Accordingly, suitable coating material may be selected from collagen, polyimide, parylene, hyaluronic acid, polyethylenglykol (PEG), poly(lactic acid) (PLA), poly(glycolic acid) (PGA), poly(lactid-co-glycolic acid) (PLGA), gelatin, hydrogel, or a bioadhesive. Said coating material may confer additional functionalities or advantageous properties to the array. E.g., coating materials may be provided with therapeutic agents or cells. Soft, viscous and flexible coatings may further protect the brittle electrically stimulating, preferably photosensitive, elements from damage, and avoid mechanical stress or trauma for the delicate target cells/tissues during or after implantation. The coating may be contiguous (i.e. cover/surround the embedded array entirely) or non-contiguous (i.e. cover only parts of the embedded array). The coating may preferably be biocompatible and optionally biodegradable as described herein in the context of substrates. The coating may preferably electrically non-conductive. The coating may comprise notches or holes. The coating may, optionally independently from the substrate, be opaque, translucent or transparent. It may be colored, wherein its upper and lower surface may be colored differently.

Collagen is a preferred biodegradable substrate or coating material as it is a biomaterial (and thus biocompatible), it can be deposited in thin membranes, and its stiffness and resorption rate can be easily tuned (Shoseyov et al. Bioengineered. 2014 January-February; 5(1):49-52). Advantageously, collagen has the potential to promote healing of the surrounding tissue and prevent fibrosis. Polyimide and parylene are preferred non-biodegradable substrate or coating materials as these are biocompatible materials, they can be deposited in thin membranes and they can have the appropriate flexibility.

Accordingly, the inventive array may preferably comprise a substrate which comprises or consists of parylene. Said substrate may preferably be configured as a film or membrane. The photosensitive elements of the inventive array are preferably disposed on said parylene film or membrane.

Alternatively, the inventive array may preferably comprise a substrate comprising or consisting of collagen. Said substrate may preferably be configured as a capsule. The photosensitive elements of the inventive array are preferably disposed within the collagen capsule.

Furthermore, inventive arrays as described herein may comprise a collagen coating.

Array Design

The inventive array and its elements—i.e. at least one electrically stimulating, preferably photosensitive, element and its substrate—may be assembled or configured in any suitable way that enables its desired applicability (e.g. as a retinal implant) and preferably exhibits at least one of the beneficial properties exemplified herein. The term "array design" in particular refers to (1) the arrangement of the electrically stimulating, preferably photosensitive, elements in or on the substrate and (2) the shape or form of the resulting array (which may typically be interdependent).

Arrangements

The inventive array may preferably comprise a plurality of at least two electrically stimulating, preferably photosensitive, elements (or "chips"). Preferably, the inventive array may comprise at least two, three or four electrically stimulating, preferably photosensitive, elements. Said electrically stimulating, preferably photosensitive, elements, may be arranged in or on said substrate in a way allowing them to exert their desired function.

Generally, any type of electrically stimulating, preferably photosensitive, elements may be arranged in or on a suitable substrate to form the inventive array. Typically, electrically stimulating, preferably photosensitive, elements, may exhibit a side length or diameter of at least 0.5 mm, 1 mm, 1.5 mm, 2 mm, 2.5 mm, 3 mm or 3.5 mm.

In the inventive arrays, electrically stimulating, preferably photosensitive, elements, may be disposed in or on the substrate at a distance of at least 0 mm, more preferably 0.01 mm, 0.05 mm, 0.10 mm, 0.20 mm, 0.25 mm, 0.30 mm, 0.50 mm, 0.60 mm, 0.70 mm, 0.80 mm, 0.90 mm or 1.0 mm from one another.

The at least two electrically stimulating, preferably photosensitive, elements, may be disposed in or on the substrate substantially linearly, in a serpentine, circularly, triangularly, quadrangularly, pentagonally, hexagonally, heptagonally, octagonally, in regular or nonregular tiling patterns, honeycomb pattern, grid pattern, filled or non filled patterns, uniform or non-uniform patterns, or arbitrarily/asymmetrically, preferably provided that the resulting array is functional, as described herein.

The choice of a suitable arrangement may inter alia depend the shape of the electrically stimulating, preferably photosensitive, elements (e.g. circular, quadrangular, hexagonal) and the desired (or required) overall shape of the resulting array. It may be preferred that the electrically stimulating, preferably photosensitive, elements, are disposed in or on the substrate linearily (i.e., in one or several rows). It may be preferred that the electrically stimulating, preferably photosensitive, elements, are disposed in or on the substrate with regular tiling patterns such as honeycomb pattern or grid pattern. A "substantially" linear, circular, elliptical, triangular, quadrangular, pentagonal, hexagonal, heptagonal, octagonal or asymmetrical shape or arrangement means that the shape or arrangement corresponds to a large degree to the indicated geometry but may comprise minor deviations therefrom.

In supported, embedded or coated arrays, the electrically stimulating, preferably photosensitive, elements may be disposed in or on the substrate in a way that their lateral margins or area is completely enclosed by (i.e. does not extend beyond) the lateral margins or area defined by the substrate. In consequence, the lateral margins or area of the inventive array as a whole may be defined by the dimensions of the substrate. It will be understood that in embedded and coated arrays, the substrate/coating typically surrounds not only the lateral margins but also at least one of the top side or bottom side of the electrically stimulating, preferably photosensitive elements.

Alternatively, in supported or coated arrays, the electrically stimulating, preferably photosensitive, elements may be disposed on the substrate in a way that their lateral margins or area is not entirely enclosed/surrounded by (i.e. extends beyond) the lateral margins or area defined by the substrate. In consequence, the lateral margins or area of the inventive array as a whole may be defined by the dimensions of the substrate and the electrically stimulating, preferably photosensitive, elements disposed thereon insofar as said elements extend beyond the area defined by the dimensions of the substrate.

Shape of the Array

The inventive array itself may have any shape which preferably facilitates its manufacturing and intended use and function (e.g. as a retinal implant). Generally, the shape of the array may or may not conform to the arrangement of electrically stimulating, preferably photosensitive, elements (e.g. which may be arranged substantially linearly, circularly, triangularly, quadrangularly, pentagonally, hexagonally, heptagonally or octagonally, honeycomb pattern, grid pattern or arbitrarily/asymmetrically). Photosensitive arrays according to the invention may thus have a substantially linear, circular, elliptical, triangular, quadrangular, pentagonal, hexagonal, heptagonal, octagonal or asymmetrical shape.

The choice of a suitable shape of the overall inventive array may inter alia depend on its desired application. For instance, in case of implantation into the human eye, the inventive array may preferably have a substantially elongated shape (i.e. which may be linear or curved in an S-form, wherein or whereon the electrically stimulating, preferably photosensitive elements are disposed in one or several rows, serpentines or displaced relatively to each other in an elongated fashion) or a substantially round or elliptical shape. It may be preferred that the electrically stimulating, preferably photosensitive, elements are disposed in or on the substrate in a linear fashion (in one or several rows, optionally displaced relatively to each other in an elongated fashion) or in a serpentine, and that the resulting array itself has a substantially elongated, linear or crooked shape.

The electrically stimulating elements, preferably photosensitive array according to the invention may have any side length or diameter that preferably enables implantation into a body part of interest (e.g. the sub- or epiretinal space of an eye) and stimulation of target cells/tissues in situ. Substantially elongated, linear or crooked shapes enable retinal implantation through small incision and facilitate horizontal placement of the array on or under retina.

The side length/diameter inter alia depends on the size and number of electrically stimulating, preferably photosensitive, elements, comprised by the array, and the space between individual photosensitive elements of the array. Specifically, the inventive array may have a side length or diameter of at least 1.5 mm, 2 mm, 2.5 mm, 3 mm, 3.5 mm, 4 mm, 4.5 mm, 5 mm, 5.5 mm, 6 mm, 6.5 mm, 7 mm, 7.5 mm, 8 mm, 8.5 mm, 9 mm, 9.5 mm, or 10 mm.

The macula, i.e. the central portion of the retina used for high resolution vision measures about 2 mm in diameter. Accordingly, arrays of the invention used as retinal implants may have dimensions that are suitable to cover the macula. For instance, in case a photosensitive array having preferably squared or round form, the side length and width may range from 2×2 mm to 10×10 mm, in particular from 3×3 mm to 5×5 mm.

The inventive array may be planar or may be pre-curved to match the shape of the retina (to that end, the array may for instance take the form of a sphere).

The electrically stimulating, preferably photosensitive array may further comprise points, barbs, hooks, and/or tacks to attach the array to the retinal tissue. The electrically stimulating, preferably photosensitive array may further comprise a handle in order to facilitate handling and alignment of the array(s), e.g. during surgery. Such a handle may for instance be formed from an elongated portion of a suitable substrate material wherein/whereupon no electrically stimulating, preferably photosensitive, elements are disposed.

In preferred embodiments, the electrically stimulating, preferably photosensitive, array (5) of the invention may thus comprise an array of a plurality of two, three, four or more electrically stimulating, preferably photosensitive elements (50), each element (50) comprising at least one, preferably a plurality of pixel arrays (1) as described herein, wherein said elements (50) are disposed on a substrate (20). Preferably, said substrate may be configured as a film or a membrane. Preferably, substrate (20) may support the plurality of elements (50). Preferably, substrate (20) may consist of a flexible, biocompatible and/or electrically nonconductive material. Preferred materials include parylene, polyimide, polydimethylsiloxane (PDMS), polyester or a polymer including polylactic acid) (PLA), poly(glycolic acid) (PGA), poly(lactid-co-glycolic acid) (PLGA) or a bioadhesive. In some preferred embodiments, array (5) may further comprise a coating (22, 22'). Preferably, coating (22, 22') may consist of a flexible, biocompatible and/or electrically non-conductive material. Optionally, coating (20, 22') may consist of a biodegradable or non-biodegradable material, or both. Preferred materials include collagen, hyaluronic acid, polyethylenglycol (PEG), poly(lactic acid) (PLA), poly(glycolic acid) (PGA), poly(lactid-co-glycolic acid) (PLGA), gelatin, or hydrogel or a biological adhesive.

In alternative, equally preferred embodiments, the electrically stimulating, preferably photosensitive, array (5) of the invention may comprise an array of a plurality of two, three, four or more electrically stimulating, preferably photosensitive elements (50), each element (50) comprising at least one, preferably a plurality of pixel arrays (1) as described herein, wherein said elements (50) are disposed in a substrate (20). Preferably, said substrate may be configured as a capsule. Preferably, elements (50) may be embedded in said substrate (20). Preferably, substrate (20) may consist of a flexible, biocompatible and/or electrically nonconductive material. Preferred materials include collagen, hyaluronic acid, polyethylenglycol (PEG), poly(lactic acid) (PLA), poly(glycolic acid) (PGA), poly(lactid-co-glycolic acid) (PLGA), gelatin, or hydrogel or a biological adhesive. In some preferred embodiments, array (5) may further comprise a coating (22, 22') as described in the context of the embodiment above.

Photosensitive Elements

The present invention provides photosensitive arrays comprising photosensitive elements. A "photosensitive element" comprised by the inventive array preferably comprises at least one "pixel" comprising at least one diode, a stimulating electrode, and preferably a counter electrode and a resistor. Preferably, said resistor may be provided between the stimulating electrode and the counter electrode. The diode(s) and resistor may preferably be electrically connected in parallel with each other. Individual pixels may be arranged in pixel arrays. Trenches may be provided between the individual diodes of a pixel and/or between the pixels of the pixel array in order to isolate those specific areas from one another. Electrical contacts between the diodes and the electrodes may be provided for establishing an electrical connection. Photosensitive elements of the inventive arrays therefore comprise a stimulating (or "working") electrode, and optionally a counter (or "return") electrode and a (shunt) resistor provided in an electrical circuit between the electrodes. The resistance of the resistor may preferably be determined according to a predetermined relation of resistance, a size of the stimulating electrode, and a size of the at least one diode, e.g. as described herein.

Preferably, the inventive array may be implanted in a sub-retinal manner with light coming from the front side of the array. Electrodes and diodes of each photosensitive element may face the side towards retina bipolar cells and incoming light. Alternatively, diodes and electrodes may be positioned on opposing sides of the photosensitive element. Photosensitive elements may thus preferably include diodes on the front side and electrodes on the back side of the element or alternatively vice versa. Alternatively, the inventive array may be implanted in an epi retinal manner with light coming from the front side and electrodes facing retina ganglion cells on the back side.

Each photosensitive element of the inventive array may comprise at least one "pixel" (i.e. assembly of diode(s) and stimulating electrode, and optionally counter electrode and resistor as described above) or a plurality of pixels. The plurality of pixels may be arranged in at least one pixel array. A "pixel array" is understood as a definite matrix or grouping of adjoining pixels. E.g., individual pixels having a hexagonal shape may be assembled into a pixel array such that one pixel is adjacent to six further surrounding pixels. The inventive array comprises a plurality of photosensitive elements, each preferably comprising or consisting of at least one, preferably a plurality of, pixel arrays.

Photosensitive elements comprised in the array of the invention may further comprise a front surface and a back surface and thus photosensitive elements comprised by the photosensitive array of the present invention may correspond to the photosensitive elements described in WO2016206809, which is incorporated by reference herein in its entirety.

Similarly, photosensitive elements comprised in the array of the invention may further comprise a substrate layer and an interface layer, and thus photosensitive elements comprised by the photosensitive array of the present invention may correspond to the photosensitive elements described as "implants" in WO 2017/045756 A1, which is incorporated by reference herein in its entirety.

When referring to the "size" of an electrode or diode or pixel (or other component of the photosensitive elements or photosensitive arrays described herein), reference is made to its spatial dimensions. Specifically, the "size" of a component of the photosensitive elements or photosensitive arrays described herein may be its a surface area, visible area, active area or else. The "size" of such a component may be indicated in relative or in absolute terms. E.g., the "size" of a diode or electrode may be indicated in absolute numbers (e.g. by referring to its visible/surface/active area) or its respective share of the total size (e.g. visible/surface/active area) of the pixel, photosensitive element, photosensitive array, etc.). When referring to the "pixel size" herein, reference is preferably made to the "pixel pitch", i.e. the size of one pixel+the size of the gap between adjacent pixels. Preferably, there may be (essentially) no gap between the pixels of a pixel array, and thus the pixel size may preferably correspond to the pixel pitch.

Resistor

Each of the electrically stimulating, preferably photosensitive, elements of the inventive array may preferably comprise a resistor, preferably positioned between the stimulating electrode and the counter electrode of said element. The resistor is preferably electrically connected in parallel to the diode(s) of said pixel. The resistor may be a shunt resistor, a wrapped resistor or another type of resistor (e.g. a resistor with indefinite resistance), although shunt resistors may be preferred. Choice of a suitable resistor may depend inter alia on the geometry of the pixel(s) of each electrically stimulating elements, preferably photosensitive element of the inventive array (and diode(s) and electrodes comprised thereby). In preferred embodiments, photosensitive elements comprised by the photosensitive array of the present invention correspond to the photosensitive elements described in WO 2016/180517 A1, which is incorporated by reference herein in its entirety. In another preferred embodiment, photosensitive elements comprised by the photosensitive array of the present invention correspond to the photosensitive elements described in WO 2016/180535 A1, which is incorporated by reference herein in its entirety.

Diode (Photo-)diodes are frequently used photodetectors. They are typically semiconductor devices which contain a p-n junction, and often an intrinsic (undoped) layer between n and p layers. Diodes with an intrinsic layer are called p-i-n or PIN photodiodes. Light absorbed in the depletion region or the intrinsic region generates electron-hole pairs, most of which contribute to an electrical current (photocurrent). Typically semiconductor materials used in (photo-)diodes include silicon (Si), germanium (Ge), indium gallium arsenide phosphide (InGaAsP), and indium gallium arsenide (InGaAs).

The size of the diode preferably determines (together with the size of the stimulating electrode) the resistance of the resistor provided in each pixel of the inventive array. In this context, the “size” of the diode preferably corresponds to its “active (diode) area” (i.e. its light-sensitive/photosensitive area).

Each pixel (and thus each photosensitive element of the inventive array) preferably comprises at least one diode. Therefore, each pixel (and thus each photosensitive element of the inventive array) may comprise 1, 2, 3 or more diodes. The diodes are preferably configured and positioned in any suitable manner that allows them to exert their desired function as described herein. The diode(s) is/are preferably connected to the stimulating electrode and to the counter electrode with either anodal or cathodal polarities.

In case each pixel (and thus each photosensitive element of the inventive array) comprises a plurality of diodes, the “diode size” preferably corresponds to the “effective diode size”, which is preferably determined by calculating the ratio of the total diode size (e.g. total diode active area) divided by the number of diodes in the pixel. The “effective diode size” may therefore correspond to the average diode size within the pixel—in particular when individual diodes of the photosensitive element have the same or a similar size. However, individual diodes of the photosensitive element may also differ in size. In such cases, other definitions for the “effective diode size” may be applied, e.g. the effective diode size may correspond to the size (e.g. diode active area) of the smallest diode present in the photosensitive element (in particular when the diodes are connected in series), or the effective diode size may be defined as the weighted average with respect to shape and position of the diode in the photosensitive element.

The diode size (preferably diode active area) may be up to 100000 $\mu m^2$. In particular, the diode size (preferably diode active area) may be between 50 $\mu m^2$ and 10 0000 $\mu m^2$. It may be preferred that the diode size (preferably diode active area) is 100 $\mu m^2$ or more, preferably 200 $\mu m^2$ or more. It may be particularly preferred that the diode size (preferably diode active area) is between 500 $\mu m^2$ and 10000 $\mu m^2$.

Stimulating Electrode

Each of the electrically stimulating, preferably photosensitive, elements, forming the array of the invention comprises a stimulating electrode (or active electrode), which is preferably configured and arranged in a way that allows them to transmit an electrical stimulus to target cells/tissues in body parts of interest (e.g. the eye) upon implantation of the inventive array. Once implanted, the stimulating electrodes are thus preferably placed in contact with the target cells/tissues, as defined above (i.e. may or may not directly contact said cells/tissues).

For electrically stimulating, preferably photosensitive arrays, used as retinal implants (preferably sub-retinal implants), stimulating electrodes of the inventive array typically directly contact at least one of individual cells, groups of cells, portions of cells and nerve fibers of the neuroretina upon implantation.

The size of the stimulating electrode preferably determines (together with the size of the diode) the resistance of the resistor preferably provided in each pixel (and thus each electrically stimulating #, preferably photosensitive element) of the inventive array. In this context, the “size” of the stimulating electrode preferably corresponds to its “active (electrode) area” (i.e. its electrically active area able to produce electricity from the supplied photocurrent).

Typically, the stimulating electrode comprises platinum, iridium oxide and/or titanium nitride. Alternatively, iridium, platinum iridium, doped diamond or diamond-like carbon or PEDOT:PSS, or other known materials may be used as electrode material. Preferred electrode materials include highly porous structures, such as a porous or fractal TiN or platinum structure (also referred to as “black platinum” or “porous platinum”). The thickness of the electrodes may vary from about 3 μm to 100 nm.

The electrode size (preferably electrode active area) may be up to 100000 $\mu m^2$ or even more. The electrode size (preferably electrode active area) may be between 5 and 10 $\mu m^2$. Alternatively, the electrode size (preferably electrode active area) may be 20 $\mu m^2$ or more, more preferably 50 $\mu m^2$ or more, even more preferably 100 $\mu m^2$ or more. It may be even more preferred that the electrode size (preferably electrode active area) is between 100 $\mu m^2$ and 10000 $\mu m^2$. It may be most preferred that the electrode size (preferably electrode active area) is between 500 $\mu m^2$ and 3300 $\mu m^2$.

For instance, a pixel comprising an electrode with an electrode active area of 5 $\mu m^2$ may for instance have a total pixel area of about 20 $\mu m^2$. The electrode size (preferably electrode active area) may be selected independently from the pixel size. It may be between 2% and 50% of the pixel size (or in particular pixel area), preferably between 5% and 20%, more preferably between 10% and 15%. Specifically, the electrode size (or in particular electrode area) may be 12.5% of the pixel size (or in particular pixel area).

The choice of suitable electrode sizes (preferably electrode active areas) is within the skill and knowledge of the skilled person in the art. For instance, smaller electrodes (e.g. with a smaller electrode active areas) may be chosen for a more precise stimulation of target cells/tissues, whereas larger electrodes (with larger electrode active areas) may facilitate manufacturing.

Neural stimulation imposes special requirements on the stimulating electrodes used for the delivery of the photocurrent. In principle, stimulating electrodes should preferably be capable of handling large current and charge densities for optimal signal processing and stimulation. However, these may also come along with degradation of the electrodes and damage to the surrounding cells/tissues. It may thus be required to reduce charge densities by increasing electrode sizes (or preferably active areas) and thereby minimize the risk of damage to the target tissue/cells or electrode itself. Therefore, the electrode size (preferably electrode active area) may sometimes be up to twice the size (preferably active area) of an electrode that would ensure an optimal charge input.

Generally, the size (preferably active area) of diode and/or stimulating electrodes of the electrically stimulating, preferably photosensitive, elements forming the array of the invention may be varied. Said sizes (preferably active areas) may be subject to upper limits as determined by the anatomical and physiological conditions or characteristics of the body part envisaged for implantation of the array (e.g. the eye) and/or the handling requirements during surgery. Lower limits for said sizes (preferably active areas) may be determined by technical limitations during manufacturing and/or also the handling requirements during surgery.

Counter Electrode

The electrically stimulating, preferably photosensitive, elements of the inventive array may further preferably comprise a counter electrode (also referred to as a "return electrode" or "ground electrode"), which provides a return current path for the stimulation signals transmitted by the stimulating electrode.

The counter electrode is preferably configured and positioned in a way that allows it to exert its desired function. For instance, the counter electrode may (preferably completely) laterally encircle (i.e. peripherally surround) the stimulating electrode and/or the diode(s) (or their respective active areas) of the photosensitive element. In case the photosensitive element comprises a plurality of diodes, the counter electrode may laterally encircle one or all of these diodes. The described arrangement(s) preferably enable improved light detection and stimulation with homogeneous field distribution of the electric field created by the stimulating electrode. The counter electrode may also encircle the stimulating electrode or the at least one diode only partially (or their respective active areas) only partially.

The size of the encircling counter electrode(s) (which preferably corresponds to its lateral expansion/width, or its respective share of the total pixel area) depends on the arrangement of stimulating electrode and diode(s) of the photosensitive elements forming the inventive array. For instance, its width can range from e.g. 1% to 30% of the pixel size. In absolute numbers, its width preferably ranges from 5 μm to 25 μm.

As an alternative, a central return electrode may be placed separate from the pixel 10, for instance at a position at a remote location on the photosensitive element. Such a configuration may also be referred to as a monopolar configuration. It is to be noted that the return electrode does not necessarily have to be in a geometrical centre of the element. Further, it is possible that a plurality of such central return electrodes are distributed over the photosensitive element. It will be understood that the present invention may be suitably used for either of these configurations.

Resistance

In preferred embodiments of the present invention, the predetermined relation of the resistance of the resistor preferably present in the electrically stimulating, preferably photosensitive, elements of the inventive array is determined by the relation of the "diode size" to the "electrode size" according to the relation:

$$R \sim D^{m} \cdot E \quad \text{(Eqn. 1)}$$

wherein

R is the resistance of the (shunt) resistor in [kOhm],

D is the diode size in [μm],

E is the electrode size in [μm], m is an exponent.

According to preferred embodiments, the above relation according to Eqn. (1) may be represented in more detail by the relation according to Eqn. (2):

$$R = a \cdot D^{n}_{area} \cdot E_{area} \quad \text{(Eqn. 2)}$$

wherein

R is the resistance of the shunt resistor in [kOhm], $E_{area}$ is the effective electrode area of the electrode in [$\mu m^2$]

n is the effective diode area of the diode in [$\mu m^2$], n is an exponent, and a is a constant.

The parameters a and n have dimensions corresponding to the dimensions of the physical parameters of the respective pixel, the pixel array and the electrically stimulating, preferably photosensitive element, as indicated in Eqn. (2a) below:

$$[\text{kOhm}] = [\text{kOhm} \cdot \mu m^{-2(n+1)}] \cdot [(\mu m^2)^n] \cdot [\mu m^2] \quad \text{(Eqn. 2a)}$$

In Eqn. (2), the exponent n is dimensionless. It will however be understood that the present approach is not a mathematical description of a pixel or of its properties. Rather, Equations (1) and (2) above allow to define implants having pixels or a pixel array with specific technical properties, which may be best reflected with the parameters indicated above. That includes that the constant a, depending on the magnitude of the exponent n may have non-integer dimensions. So far, the inventors could not come up with a satisfying physical explanation of this phenomenon. This, however, has no influence on the suitability of the parameters to define the present invention, i.e. the implant and, in particular, the technical properties of the at least one pixel or an entire pixel array.

The exponent n and the constant a generally determine the interrelation between diode size, electrode size and resistance. Electrically stimulating, preferably photosensitive elements (and arrays comprising the same) designed according to these parameters are considered advantageous over the vast amount of possible other, arbitrary sets of parameters, and may thus be better suited as (retinal) implants. Such implants may exhibit an increased performance as compared to other implants that do not comprise an array with electrically stimulating, preferably photosensitive elements defined by the respective parameters as indicated herein. That identified relation in particular also provides a way to predict optimal shunt resistors and therefore to facilitate the production of the electrically stimulating, preferably photosensitive elements forming the photosensitive arrays of the invention.

The electrode size may be chosen such that, for a predetermined total diode active area, the ratio between the total diode active area and the electrode area is between 0.1 and 10, preferably between 1 and 9, most preferably between 3 and 6. Electrically stimulating, preferably photosensitive elements comprising pixels with such electrode areas may be particularly advantageous in that they may provide maximized charge density without decreasing electrode performance in terms of charge balancing.

Alternatively, the electrode size (preferably electrode active area) may be chosen such that, for a predetermined diode active area, in the relation between diode active area and electrode active area the constant a is chosen from the interval [$3 \cdot 10^5$; $2 \cdot 10^6$]. Preferably, the constant a may be chosen from the interval [$7 \cdot 10^5$; $1.5 \cdot 10^6$]. More preferably, a may be $10^6$.

Specifically, the constant a may be $10^6$ and the exponent n may be chosen from the interval [−1.5; −2], preferably from the interval [−1.75; −1.85].

Alternatively, the electrode size (preferably electrode active area) may be chosen such that, for a predetermined diode active area, in the relation between diode active area and electrode active area the exponent n may be chosen from the interval [−1.5; −2]. Preferably the exponent n may be chosen from the interval [−1.75; −1.85]. More preferably, n may be −1.81.

Specifically, the exponent n may be −1.81 and the constant a may be chosen from the interval [$3\cdot10^5$; $2\cdot10^6$], preferably from the interval [$7\cdot10^5$; $1.5\cdot10^6$].

With respect to the shunt resistor values, values may differ from the indicated values e.g., from 10% of the represented value up to ten times the optimum value, preferably from 50% of the value up to 5 times the value represented.

Parameters within the above-recited ranges preferably enables the provision of the electrically stimulating, preferably photosensitive, elements described herein. In particular, electrically stimulating, preferably photosensitive, elements comprising (shunt) resistors characterized by the recited values for the constant a and/or the exponent n preferably exhibit multiple advantageous characteristics in terms of e.g. both charge injection and charge balancing, whereas other approaches may improve electrically stimulating elements, preferably photosensitive element characteristics with respect to only one of both parameters. The described approach therefore advantageously enables a multi-parameter assessment and the provision of electrically stimulating, preferably photosensitive, elements and arrays comprising the same exhibiting favorable properties, specifically when implanted and placed in contact to target tissue/cells.

As is known to those skilled in the art, the exact values of electrode/diode size and resistance still comprise tolerances. That is due to the fact that further parameters, which are not viable to the scope of the described approach, may require further compromises regarding the final structure of the implant. The approach described herein thus provides a range of resistance values that are acceptable for effective implantable electrically stimulating elements, preferably photosensitive arrays within the scope of the present invention.

Further Extra- or Intraocular Devices

Electrically stimulating, preferably photosensitive arrays according to the invention may be used with additional extra- or intraocular devices.

Electrically stimulating, preferably photosensitive arrays used as sub-retinal implants should in principle replace dysfunctional layers of the neuroretina and integrate into the natural circuitry of the eye without requiring any additional power supply or signal conversion. However, sub-retinal implants may also further incorporate a device for capturing a signal representing the image information, such as a video camera, and a sender relaying the signal to the array via wires, or by a wireless link.

For instance, the sender may send signals proportional to sensed incident light via hardwiring into the sub-retinal space, where the inventive array is be placed. Alternatively, received image information can be transmitted to the implant via electromagnetic induction. For that purpose, radio frequency (RF) energy transmitted from an external power source can be employed to send signals to a coil located in the eye that is in communication with the stimulation and ground electrodes (cf. U.S. Pat. No. 4,628,933 A).

Preferably, electrically stimulating, preferably photosensitive arrays according to the invention may be supplied via invisible infrared radiation which is converted into electrical energy by means of infrared-sensitive photodiodes (cf. WO 98/17343 A1). Such implants typically additionally comprise glasses (optionally equipped with a video camera receiving the image information) converting visible light to infrared light. Advantageously, for a given energy level, infrared is less harmful than visible light, and does not require hardwiring. The glasses ensure amplification of the image in low light and on the contrary attenuation under strong light, and facilitate functioning of the artificial retina over a broader luminosity range.

Accordingly, a (sub-)retinal implant employing the inventive array may inter alia incorporate an additional light source. Such light sources may in principle be external or internal to the body. Light sources may for instance emit (optionally pulsed) infrared light (IR) and in particular near-infrared light (NIR) to excite the diodes of the inventive array while remaining invisible to any remaining photoreceptors in the retina. Upon exposure to the incident light, diodes in each pixel of the sub-retinal array convert this light into pulsed current which stimulates the neuroretina. Specifically, a pocket computer may process images captured by a miniature video camera. A near-to-eye projection system projects these images into the eye and onto a photodiode array using (pulsed) IR, in particular NIR (e.g. 880-915 nm) light. (N)IR light has the advantage of being capable of penetrating through several tissue layers (e.g. skin or others), however, the electrically stimulating, preferably photosensitive array of the invention is not limited to the use in connection with (N)IR light.

Pixels comprising shunt resistors may particularly advantageous when utilizing the inventive arrays as sub-retinal implants in connection with via (N)IR light pulses. The shunt resistor allows both rapid discharging of the charge delivered during the first phase of the IR pulse and controlling the charge delivered to the target cells/tissues. In contrast, when a shunt resistor with a high resistance (or no shunt resistor at all) is used, discharging may be delayed—which increases the risk of insufficient charge balancing before the next IR pulse arrives. A high resistance of the shunt resistor therefore potentially limits the capacitance available for the next pulse and therefore the delivered charge in steady state would be reduced.

Manufacturing Method

A further aspect of the present invention refers to a method for producing an array as described herein. The method comprises at least the steps of (1) providing a substrate, preferably as described herein; (2) providing at least two electrically stimulating, preferably photosensitive, elements ("implants"), each comprising at least one pixel having at least one a stimulating electrode, a counter electrode, and optionally at least one diode and/or a resistor, wherein the resistance of the resistor is preferably chosen according to a predetermined relation of resistance, size of the stimulating electrode, and size of the diode; (3) disposing said electrically stimulating, preferably photosensitive, elements in or on said substrate; (4) optionally adding a optionally adding a coating, a top layer, and/or a therapeutic agent as described herein.

Electrically stimulating, preferably photosensitive elements to be arranged in the inventive array can be obtained, e.g., using the method as described in WO 2016/180517 A1. Accordingly, the electrically stimulating, preferably photosensitive elements used are preferably the ones described herein, wherein preferably the size of the stimulating electrode and the size of the diode is represented as an area of the stimulating electrode and the diode, respectively and wherein the diode size is an effective diode size represented by a ratio of a total diode size, preferably a total diode area, and the number of diodes in the pixel. Specifically, the resistance of the resistor of each pixel of said electrically stimulating, preferably photosensitive elements may preferably be determined by the formula:

$$R=a\cdot D^{n}_{area}\cdot E_{area} \quad \text{(Eqn. 2)}$$

wherein

R is the resistance of the shunt resistor in [kOhm], $E_{area}$ is the effective electrode area of the electrode in [$\mu m^2$]

$D_{area}$ is the effective diode area of the diode in [$\mu m^2$], n is an exponent, and a is a constant.

The choice of parameters and parameter sets during production of the inventive array may depend on the materials used for the substrate, the optional coating and the design of the electrically stimulating, preferably photosensitive, elements as such.

In step (3) of the inventive method, electrically stimulating, preferably photosensitive, elements may preferably be disposed in or on said substrate by (a) (fully or partially) embedding said elements in said substrate or (b) attaching said electrically stimulating, preferably photosensitive, elements to said substrate, optionally by adhesive forces or a bioadhesive.

For instance, for supported arrays (with substrates in the form of a film or membrane), step (3) of the inventive method may involve arranging the electrically stimulating, preferably photosensitive, elements as desired (e.g. in a row, with electrode sides downwards), optionally in a suitable fixture and depositing a film of the desired substrate (e.g. parylene, polyimide, PDMS, polyester, PGA, PGLA or PLA or a biological glue) on the back of the elements. In a further step, the substrate may be adjusted (e.g. cut) to assume a desired shape.

When "sandwiched" arrays with a top layer are produced, step (3) of the inventive method may involve (i) adding the top layer to the electrically stimulating array, preferably photosensitive array as a continuous layer. That continuous layer may be processed by introducing holes or notches at the sites of the electrically stimulating, preferably photosensitive, elements such that these elements are exposed to the exterior. Typically, the top layer may be provided as a mask (with holes and notches) which is placed onto the array such that the electrically stimulating, preferably photosensitive, elements protrude through the mask or are recessed within the mask such that there is a void space between the upper surface of the electrically stimulating, preferably photosensitive, elements and the upper surface of the coating. The void space may be filled with a biodegradable coating by step (4) such that the electrically stimulating, preferably photosensitive, elements are exposed to the exterior upon implantation and degradation of the filled-in coating.

When embedded arrays with "capsule-type" substrates are produced, step (3) of the inventive method may involve embedding the electrically stimulating, preferably photosensitive, elements in a suitable (sufficiently absorptive) substrate material (e.g. viscous hyaluronic acid, non-cross-linked monomers of e.g. collagen) and optionally inducing retentive properties of said material (e.g. applying a cross-linking process).

When coated arrays are produced, step (4) of the inventive method may involve (i) adding the coating to the electrically stimulating array, preferably photosensitive array as a continuous layer. That continuous layer may be processed by introducing holes or notches at the sites of the electrically stimulating, preferably photosensitive, elements such that these elements are exposed to the exterior. Alternatively, the coated array may be implanted as such or by the biodegradable coating is degraded fast or slowly such that the electrically stimulating, preferably photosensitive, elements exposed to the exterior upon implantation. Alternatively, the coated layer may be provided as a mask (with holes and notches) which is placed onto the electrically stimulating array, preferably photosensitive array such that the electrically stimulating, preferably photosensitive, elements protrude through the mask or are recessed within the mask such that there is a void space between the upper surface of the electrically stimulating, preferably photosensitive, elements and the upper surface of the coating.

Generally, the manufacturing method may inter alia depend on the substrate material and the desired configuration of the array (supported vs. embedded). An exemplary manufacturing method for silicon-based arrays may comprise eight mask layers: deep reactive-ion etching (DRIE) for in-pixel photodiode isolation, $n^+$ region doping to form the pn junction, $p^+$ region doping to make ohmic contacts, first via opening, first metal (Ti/Pt) deposition and liftoff, second via opening, removal of polysilicon in selected trenches, and second metal (iridium oxide) deposition and liftoff as described in detail in Wang et al. J. Neural Eng. 9 (2012) 046014.

The method may further include a step of adding therapeutic agents, such as therapeutic cells, gene-therapy vectors, or drugs to the substrate and/or the coating either before or after the electrically stimulating, preferably photosensitive, elements are disposed in or on the substrate or the coating is added.

Use and Function

Electrically stimulating arrays, and preferably photosensitive arrays according to the invention are envisaged (and thus preferably adapted) for (electrically) stimulating target cells or tissues, in particular neural cells, in body parts of interest. To that end, the inventive array may be implanted in a tissue or body part of interest and placed in contact with the target cells or tissues (i.e. cells or tissues that are to be (electrically) stimulated by the inventive array). The terms "electrically stimulating array" and "photosensitive array" includes arrays in implanted and non-implanted form. "Placed in contact" means that the inventive array is positioned in a way that preferably enables (electrical) stimulation of the target cells or tissues. It may involve direct or indirect contact between target cells/tissues and the inventive array, provided that the signal (electrical current) generated by said array preferably reaches and stimulates the target cells or tissues. The target cells/tissues are typically adjacent to or surrounding the array (including electrically stimulating array or photosensitive array).

The inventive array may thus be used as an implant, preferably a retinal implant, or an implant of the brain, a heart implant or an implant for any other living tissue such as of the ear, in particular the inner ear, or muscles among others, which may be electrically stimulated. The inventive array is thus preferably configured for implantation into a body part of interest, in particular an eye.

It is particularly envisaged herein to employ electrically stimulating, preferably photosensitive arrays of the invention as retinal implants or—prostheses, preferably as subretinal implants. Accordingly, the inventive array may preferably be configured for stimulation of the neuroretina (i.e. the layers of neural cells (bipolar cells, horizontal cells, amacrine cells, optionally ganglion cells and/or (remaining) photo receptor cells) within the retina), specifically in patients with age-related macular disease (AMD) or retinitis pigmentosa (RP), i.e. diseases that are characterized by a degeneration of photo receptor cells, leading to progressive loss of sight.

Once implanted into the (human) eye, the diode(s) present in each electrically stimulating, preferably photosensitive element of the array are typically excited by incident light and produce an electrical current ("photocurrent") that is transferred to the stimulating electrode(s) placed in proximity to and electrically coupled to the diode(s). Thereby, the stimulating electrode(s) is/are excited and create an electrical current that is delivered to (and thereby stimulates) target cells/tissues (e.g. surviving cells of the neuroretina, including bipolar, horizontal, amacrine, and potentially also ganglion cells). The pattern of diode(s) activated by incident light therefore stimulates a pattern of neural cells of the retina. The resulting electrical stimulation pattern that is then conveyed from the ganglion cells of the inner retina and guided via the optic nerve into the visual cortex, leading to a visual perception representative of the original incident image.

The diode(s) of the electrically stimulating, preferably photosensitive elements of the inventive array thus preferably receive incident light and generate an electrical charge in the stimulating electrode(s). In some cases, it may be preferred to provide sub-retinal implants receiving power from external circuitry to amplify the image signal. In addition, implants and in particular sub-retinal implants comprising the inventive (photosensitive) arrays may be used in connection with further extra—and/or intraocular devices, including image capturing systems and signal converters and—transmitters. Alternatively, the inventive array may be used as an epi-retinal implant and deposited on the surface of the retina facing the crystalline lense.

A electrically stimulating, preferably photosensitive array according to the invention may thus be implanted in any suitable way, as long as it is configured and positioned in a way that preferably allows the diode(s) to receive incident light, and generate and transmit an electrical current to the stimulating electrodes, which in turn transmit an electrical current to target cells or tissues to cause electrical stimulation. It is also conceivable to implant several electrically stimulating, preferably photosensitive arrays into the (human) eye, to provide for allowing to cover a larger retinal zone and thus larger visual field.

DESCRIPTION OF THE FIGURES

Further details, preferred embodiments and advantages of the present invention will be found in the following description with reference to the drawings, in which:

FIG. 1 shows an electrically stimulating (preferably photosensitive) array 5 of electrically stimulating (preferably photosensitive) elements 50 embedded in and/or supported by a substrate (20, 22, 22'). A shows a substrate supported electrically stimulating (preferably photosensitive) array 5, wherein the electrically stimulating (preferably photosensitive) elements 50 are disposed on a substrate 20. B shows an embedded/coated electrically stimulating (preferably photosensitive) array 5, wherein the electrically stimulating (preferably photosensitive) elements 50 are disposed on a substrate 20 and further embedded in and coated by further substrate materials (22, 22').

Figure 4:
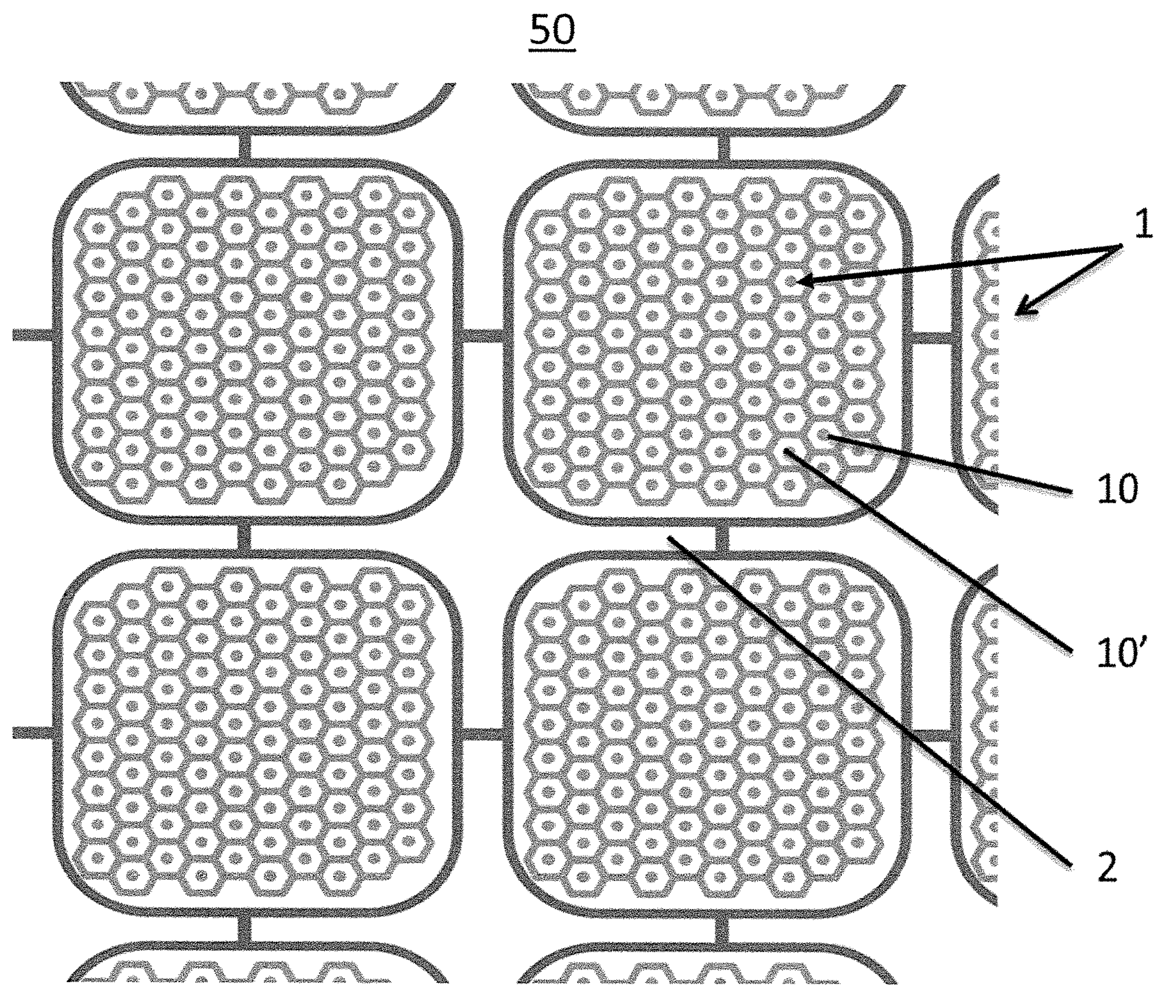
FIG. 4 displays pixel arrays 1 which may form a photosensitive element 50 as used in the inventive photosensitive array 5.

Each electrically stimulating (preferably photosensitive) element 50 of the inventive array 5 preferably comprises a plurality of pixels 10 (as exemplarily shown in FIG. 2, 3) arranged into pixel arrays 1 (as exemplarily shown in FIG. 4).

Figure 1:
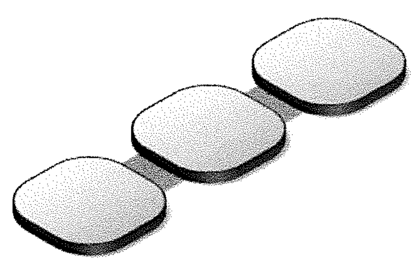
FIG. 1 is a schematic illustration of photosensitive arrays 5 according to the invention comprising three photosensitive elements 50 arranged in a row. A: Photosensitive array 5 comprising photosensitive elements 50 disposed on a film- or membrane-like substrate in 3D view (left panel) and cross-sectional view (right panel). B: Photosensitive array 5 comprising photosensitive elements 50 disposed on a capsule-like substrate in 3D view (left panel) and cross-sectional view (right panel).
Figure 1:
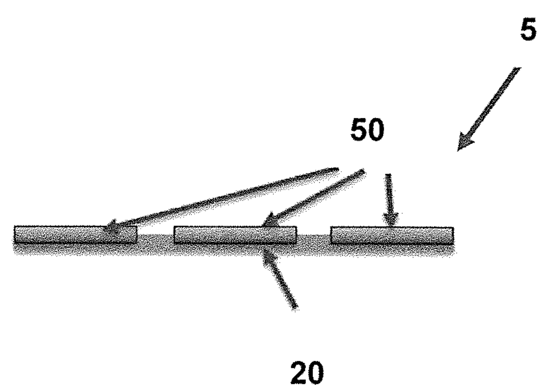
Figure 1:
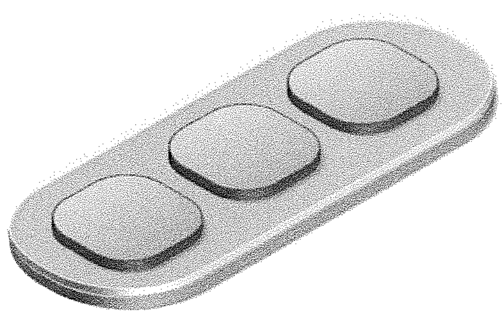
Figure 1:
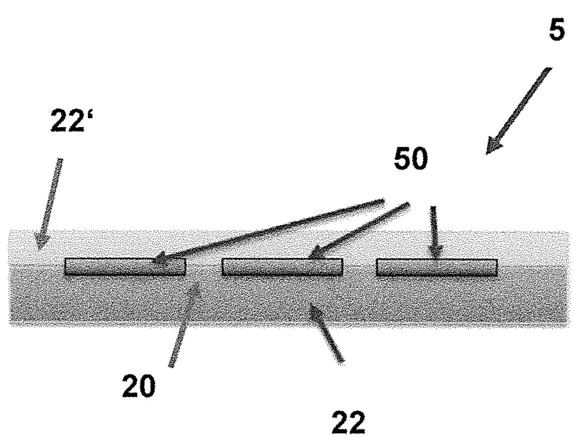
Figure 2:
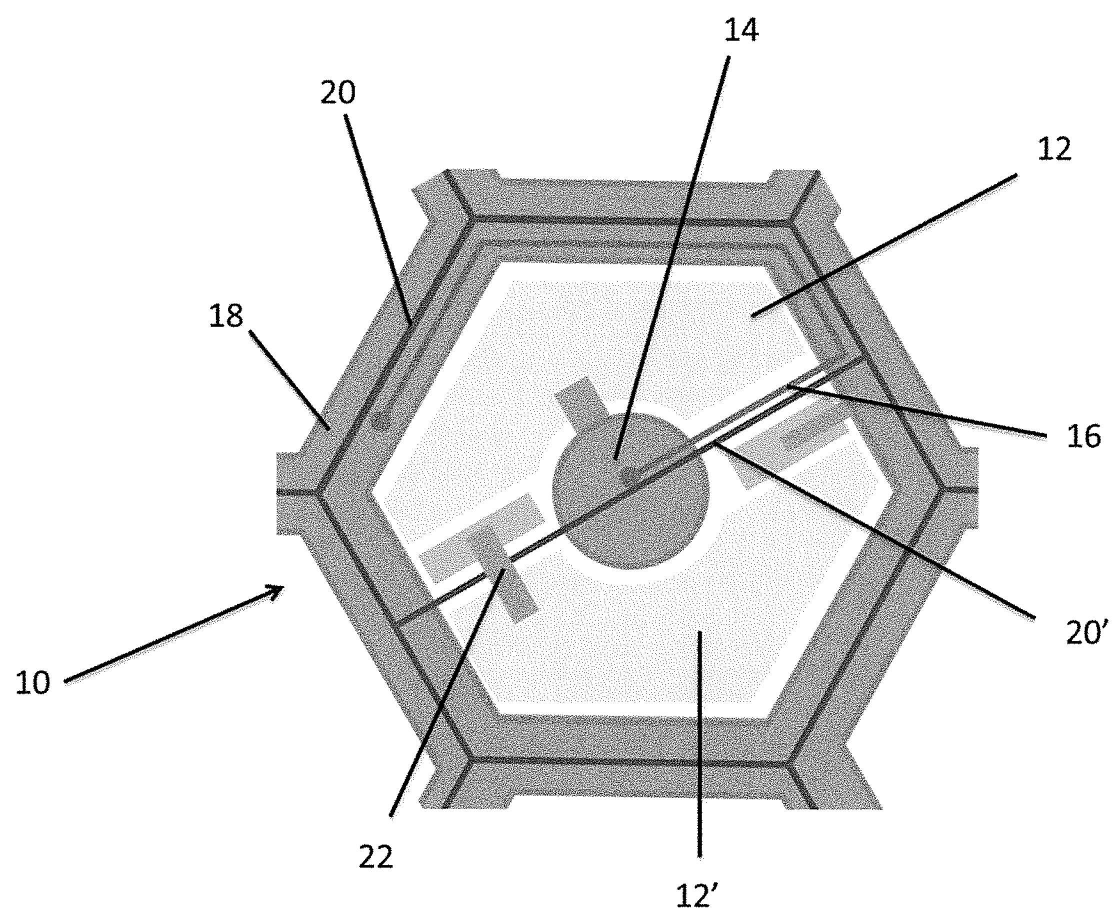
FIG. 2 is an example of a photosensitive pixel 10 with an electrode.
Figure 3:
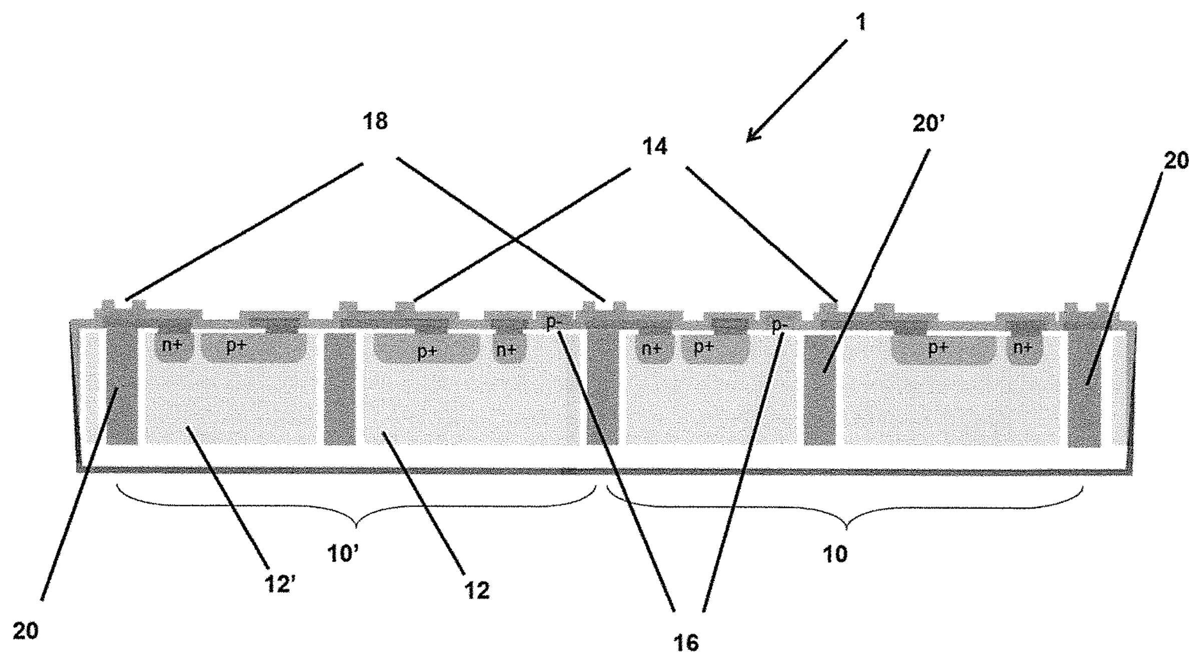
FIG. 3 is a schematic cross-sectional view of a semiconductor structure with two adjacent pixels forming a pixel array 1.

FIG. 2 shows a photosensitive pixel 10. The photosensitive pixel 10 ("pixel") comprises a photosensitive diode 12, a central electrode 14 and a resistor 16. At an outer periphery of the pixel, a counter electrode 18 ("return electrode") is provided. The counter electrode 18 can be placed on each pixel, for instance at the periphery of each pixel, as shown in FIG. 3. The return electrode is thus local and in-between the different central electrodes of a pixel array 1 ("bipolar" configuration).

In such a bipolar configuration, the return electrodes may be electrically disconnected from one another, resulting in the pixels being (operating) completely independent from one another. Alternatively, all return electrodes of individual pixels may be electrically connected, and form a grid-like structure optionally exhibiting a hexagonal pattern, which may extend over the whole pixel array 1.

As a further alternative, a central return electrode may be located separately from the central (stimulating) electrode(s). Such a central return electrode may in particular be provided at a remote location on the photosensitive element ("monopolar" configuration). The return electrode may, but does not necessarily have to be located in the geometrical centre of the photosensitive element. Further, a plurality of such central electrodes may be provided, which are distributed over the photosensitive element or the pixel array.

The pixel 10 shown in FIG. 2 has a substantially symmetric hexagonal shape. Further pixels may be provided adjacent to each of the sides of the hexagonal pixel, forming an array of pixels ("pixel array" or "electrode array") 1, as exemplarily shown in FIG. 4. Alternative pixel forms are also conceivable. For instance, pixels may have an octagonal, rectangular, circular or diamond shape or any other suitable shape. Pixels 10 are separated from each other by means of a trench 20. The trench 20 comprises an electrically isolating material. Accordingly, individual pixels 10 are preferably electrically isolated from each other. The counter electrode 18 is arranged on the trench 20 surrounding the periphery of the pixel 10.

In FIG. 3, the pixel 10 further comprises two diodes 12, 12'. The diodes 12, 12' are arranged within the hexagon defined by the pixel shape. Preferably, the diodes 12, 12' are symmetrically arranged. Between the diodes 12, 12', an isolating trench 20' is provided. The isolating trench 20' between the diodes 12, 12' has the same properties as the isolating trench 20. The diodes 12, 12' are therefore electrically isolated from each other. Electrical connections between the elements of each pixel may nevertheless be established by means of electrical contacts (cf. FIG. 2, wherein diodes are electrically connected by an electrical contact 22). In FIG. 3, the diodes are thus connected in series (cf. FIG. 5 for further details). The diodes 12, 12', and in particular their photosensitive surface area as shown in FIG. 2, represent the photosensitive area of the pixel 10. Therein, the diode surface area is essentially symmetric around a symmetry axis (not shown) of the pixel 10. The number of diodes may however also be different, e.g. the pixel 10 may comprise only one diode, which may increase the photosensitive area of the pixel 10, as in such cases the trenches 20' would be dispensable. Alternatively, pixels 10 may comprise three or more diodes. If more than two diodes are provided in a pixel, the individual diodes may also be serially connected with one another, as already discussed for a two-diode pixel above.

A plurality (e.g. two or three) of diodes may be provided in each pixel 10 to increase the voltage generated in response to the incident light. The diodes may therefore be serially connected, wherein the voltage of a number N of diodes is the factor N higher than the voltage created by one diode only. On the other hand, an increased number of diodes means that fewer light may be collected by each diode, per pixel. The electrical current created by each of those diodes connected in series may be significantly lower when having a plurality of diodes compared to having only one or a few diodes. Typically, the current in a circuit with N diodes is N times less than the current of one diode. It is therefore a matter of choice, which of the parameters, i.e., current or voltage, is more desirable for an individual application. In the specific case of neural stimulation, the required stimulation parameters may depend on the tissue and the individual neuronal cells to be excited, the position of an implant and even individual specifics of a patient, possibly age, state of disease and general physiological condition.

In the center of the pixel 10, an electrode 14 is provided. Due to its central position, said electrode 14 is also referred to as the "central electrode" (or, as it is typically used for stimulation, "stimulating electrode"). The stimulating electrode 14 shown in FIG. 3 has a circular shape. However, stimulating electrodes 14 may also have different shapes, e.g. a shape mimicking the shape of the return electrode 18 or the trench 20 conforming to the shape of the pixel 10. Circular shapes may advantageously ensure homogeneity of the electrical field generated by the stimulating electrode 14. Depending on the intended application, the stimulating electrode 14 may assume a shape enabling less homogenous, locally enhanced field distributions.

The electrode 14 of the pixel 10 may be adapted for stimulation of surrounding tissue, preferably neural tissue, in particular neural tissue of a retina in vivo. Typically, the electrode comprises platinum, iridium oxide and/or titanium nitride. Alternatively, iridium, platinum iridium, doped diamond or diamond-like carbon or PEDOT:PSS, or other known materials may be used as electrode material. Preferred electrode materials include highly porous structures, such as a porous or fractal TiN or platinum structure (also referred to as "black platinum" or "porous platinum"). The thickness of the electrodes 14 may vary from about 100 nm to 3 μm. It is, however, also possible to have an electrode thickness in the range of 10 μm as well, or below 100 nm.

In FIG. 2, the return electrode 18 is provided as an elongate electrode surrounding the pixel and conforming to the contours of its hexagonal shape. Alternatively, a plurality of return electrodes may be provided, which surround the pixel 10 and the stimulating electrode 14 in regular patterns or arbitrarily. This may in particular be exerted at a peripheral portion of a pixel array 1. Further, a (shunt) resistor 16 is positioned between the stimulating electrode 14 and the counter electrode 18. The (shunt) resistor 16 may in particular be provided on the trench between two diodes 12, 12' of the pixel 10, as is shown in more detail in FIG. 3.

FIG. 3 shows a sectional side view of a portion of a pixel array 1 with two adjacent pixels 10, 10'. The pixels 10, 10' correspond to the pixel as shown in FIG. 2, having two diodes 12, 12'. One- or three diode pixels may exhibit the same layer structure as shown in FIG. 2 for two diode pixels, mutatis mutandis. The resistor 16 may be located on the surface of the pixel. The resistor 16 may be a conductor on the surface of the pixel 10. Specifically, said conductor may comprise or consist of doped silicon, in particular lightly doped silicon. The pixel array 1 may be supported by substrate 2, as depicted in FIG. 4.

FIG. 4 shows an array of pixels 1 ("pixel array", "electrode array") comprising a plurality of pixels 10. The size of the pixels 10 may be chosen depending inter alia on the intended application of the pixel array 1. Each photosensitive element 5 typically comprises a plurality of pixels 10 arranged in a plurality of pixel arrays 1. The inventive photosensitive array may advantageously comprise photosensitive elements 5 comprising pixels 10 and pixel arrays 1 as depicted in FIG. 4.

Figure 5:
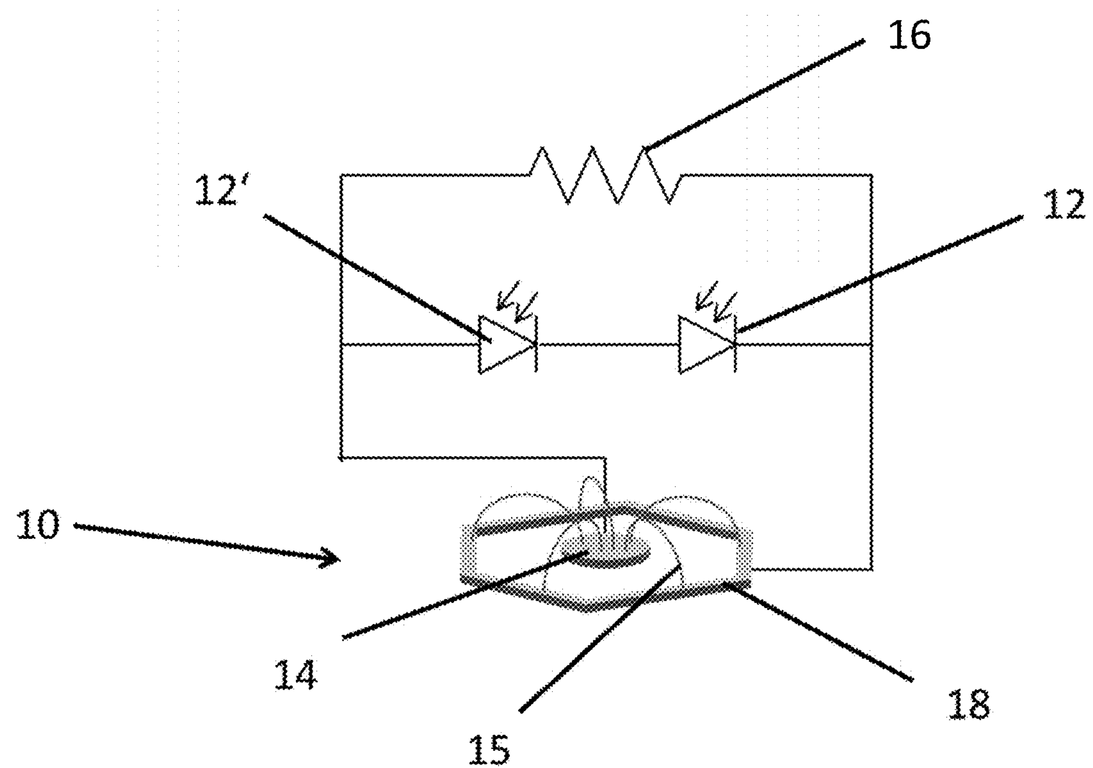
FIG. 5 is a perspective view of the photosensitive pixel of FIG. 2 with a schematic drawing of a wiring circuit.

FIG. 5 shows a schematic perspective view of a pixel 10. The return electrode 18 conforms to the hexagonal shape of the pixel. The stimulating electrode 14 is a circular electrode. If electrical voltage is applied, i.e., when the stimulating electrode generates an electrical pulse, an electrical field, represented by the electrical field lines 15 in FIG. 5, is generated. Target cells/tissues adjacent to this electrical field may eventually be stimulated, depending on the specifics of the stimulation pulse such as strength, duration polarity, and so forth. The electrode may also be placed in tissue in a way that the tissue, i.e. the cells within the tissue, may directly contact the electrode.

The pixel 10 shown in FIG. 5 further comprises two diodes 12, 12', which are serially connected, and the (shunt) resistor 16 is connected in parallel to the diodes 12, 12', thereby preferably establishing an electrical circuit with reliable charge balancing and stimulation parameters.

Figure 6:
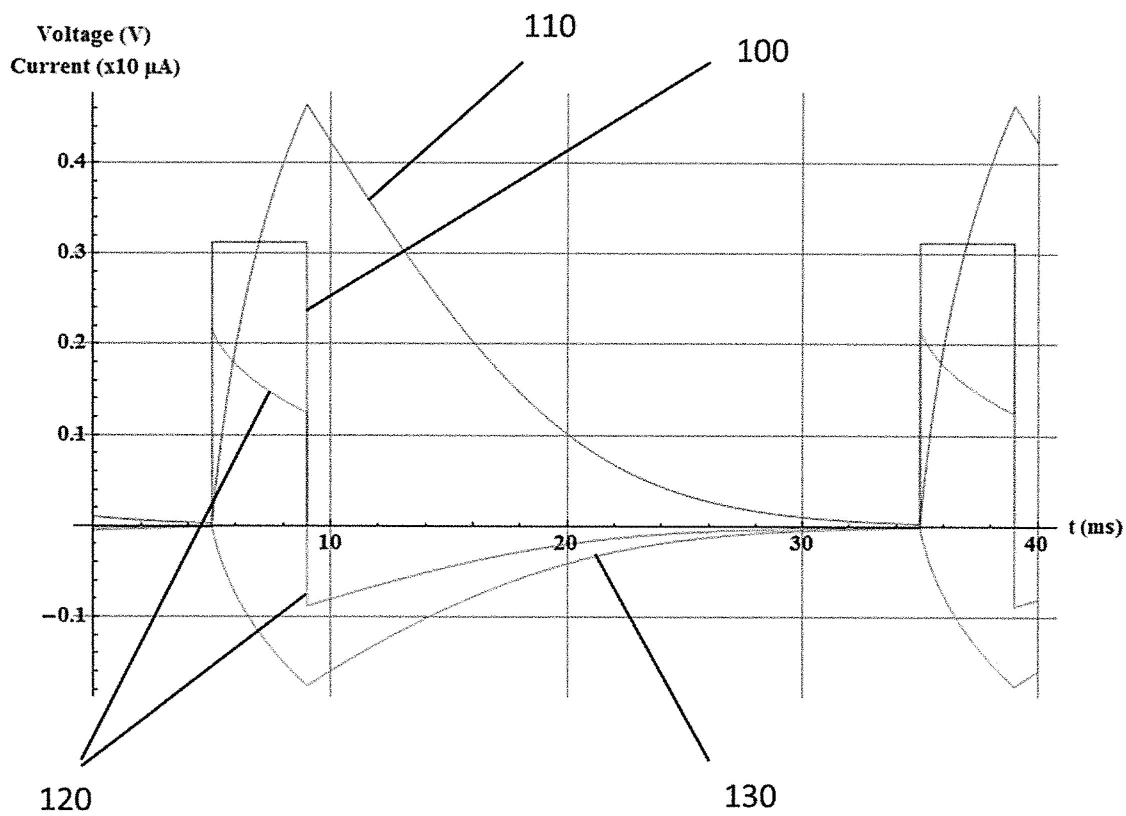
FIG. 6 is a diagram representing a stimulation pulse.

FIG. 6 illustrates the function of the employed pixels 10. An incident light pulse 100 enters the pixel 10. The light pulse may be an infrared light pulse e.g. with a wavelength ranging from 750 nm to 3000 nm, preferably between 800 nm and 1000 nm and most preferably between 830 nm and 915 nm. Preferably, the light pulse may be a square pulse.

However, sawtooth light pulses or light pulses with a non-linear ramping up and/or down of the light intensity may also be employed. Incident light pulses cause the generation of a (photo-)current 120. The longer the light pulse is applied, the higher gets the voltage 110 of the stimulation electrode 14. As the voltage on the active electrode 110 increases in the positive or negative range, the voltage of the counter electrode 130 conversely increases in the negative or positive region, for anodal or cathodal polarity, respectively.

After the light stimulation ceases, the current 120 drops and the voltages of the stimulating electrode and on the return electrode decrease. However, the voltages need time, depending primarily on the resistance of the shunt resistor 16, to equalize. In the example according to FIG. 6, the voltages have dropped to zero only about 26 ms after the light pulse ceased. Only then a next stimulating pulse with full capacitance may be applied by the respective pixel.

The resistance of the resistor 16 significantly influences the function and the performance of the pixel 10. If a light pulse is received by one of the diodes 12, 12', i.e. on the photosensitive area, the light pulse is converted into an electrical pulse. The electrical signal is delivered to the stimulating electrode 14. The charge delivered per phase for a light pulse should, ideally, be maximized, in order to increase the stimulation efficacy. The charge density, on the other hand, cannot be too high, in order to prevent tissue damage. Thus, charge densities of between 0.35 $mC/cm^2$ and 1.5 $mC/cm^2$, typically of 1 $mC/cm^2$ are generally chosen. The charge further has to discharge fast enough such that prior to a following pulse, the voltage applied may drop ideally all the way back to zero to balance the charges. This requires a low value resistor. On the other hand, a low resistance of the shunt resistor would allow the charge to discharge rapidly and fully, but a significant fraction of the photogenerated charge would be lost in the shunt resistor 16 and the charge delivered to the tissue would be reduced.

Ideally, resistances of the shunt resistor scale with the area of the stimulating area and of the photosensitive area as indicated above.

The above-mentioned findings may best be described by means of an exponent n according to the relation $-1.5<n<-2$. Preferably, the exponent n may be chosen between $-1.65<n<-1.95$, and more particularly between $-1.75<n<-1.85$. In particular, the exponent n may be $n=-1.81$.

Tables 1 and 2 provide an overview of some preferred parameter sets for the photosensitive elements assembled in the inventive array in terms of the respective areas in $\mu m^2$ of the electrodes and the diodes. That approach considering the respective areas allows to consider almost arbitrary shapes of the pixels, diodes and the electrodes.

For the parameters set out in Tables 1 and 2, it was identified that, for a preferred exponent n of $n=-1.81$ the constant a preferably lies between $3\cdot10^5<a<2\cdot10^6$. More preferably the constant a lies between $7\cdot10^5<a<1.5\cdot10^6$. In even more preferred embodiments, the constant a lies between $7.5\cdot10^5<a<1.25\cdot10^6$. The constant a may for instance be $a=10^6\pm20\%$. Most preferably, the constant a is $a=10^6\pm10\%$ in such a setting. Note that the pixel size in [μm] is a measure as commonly used in order to characterize the pixel. The pixel size itself is not considered for defining the individual characteristics of a pixel in terms of the electrode size (area), diode size (area) and resistance of the resistor. It is further to be understood that the examples provided shall only exemplify the inventive idea to define a pixel or pixel array by means of the resistance of the resistor 16, a size of the electrode 14 and a size of one or more diodes 12, 12'.

Pixel arrays with pixel-structures according to the parameter sets as set out in Table 1 were optimized for light applied with a power of about 5 $mW/mm^2$ and a light pulse duration of about 4 ms.

TABLE 1

Resistance of shunt resistor optimized for light pulses of 4 ms with light power of 5 mW/mm^2

| # of diodes | Pixel size [μm] | Electrode area [μm^2] | Resistance [kOhm] |
|---|---|---|---|
| 1 | 75 | 1650.8 | 520.6 |
| 2 | 75 | 554.8 | 1756.7 |
| 3 | 75 | 255.0 | 1543.0 |
| 1 | 100 | 3408.8 | 283.4 |
| 2 | 100 | 766.7 | 520.6 |
| 3 | 100 | 554.8 | 1296.2 |
| 1 | 140 | 7287.0 | 154.3 |
| 2 | 140 | 1650.8 | 384.1 |
| 3 | 140 | 1314.7 | 520.6 |
| 1 | 280 | 24911.0 | 45.7 |
| 2 | 280 | 7287.0 | 84.0 |
| 3 | 280 | 4536.0 | 113.8 |

Pixel arrays with pixel-structures according to Table 2 were optimized for light applied with a power of about 3 $mW/mm^2$ and a light pulse duration of about 4 ms.

TABLE 2

Resistance of shunt resistor optimized for light pulses of 4 ms with light power of 3 mW/mm^2[2]

| # of diodes | Pixel size [μm] | Electrode size [μm^2] | Resistance [kOhm] |
|---|---|---|---|
| 2 | 75 | 384.2 | 1815.4 |
| 3 | 75 | 255.0 | 3154.8 |
| 1 | 100 | 2907.2 | 345.9 |
| 2 | 100 | 766.7 | 1044.7 |
| 3 | 100 | 384.2 | 1377.1 |
| 1 | 140 | 5828.8 | 209.1 |
| 2 | 140 | 1650.8 | 520.6 |
| 3 | 140 | 1020.0 | 705.6 |

Table 3 displays parameter sets for pixels, which were identified to be a particular advantageous choice of the multitude of possible configurations. The parameter sets as set out in Table 3 were optimized for light applied with a power of about 5 $mW/mm^2$ and a light pulse duration of about 4 ms

TABLE 3

Preferred resistance of shunt resistor optimized for light pulses of 4 ms with light power of 5 mW/mm^2[2]

| # of diodes | Pixel size [μm] | Electrode area [μm^2] | Resistance [kOhm] |
|---|---|---|---|
| 2 | 75 | 384.2 | 1800 |
| 1 | 100 | 1650.8 | 250 |
| 2 | 100 | 766.7 | 900 |
| 3 | 100 | 384.2 | 1200 |
| 1 | 140 | 5828.8 | 130 |
| 1 | 140 | 2447.0 | 130 |
| 2 | 140 | 2907.2 | 450 |
| 2 | 140 | 1650.8 | 400 |
| 3 | 140 | 1020.0 | 600 |

Figure 7:
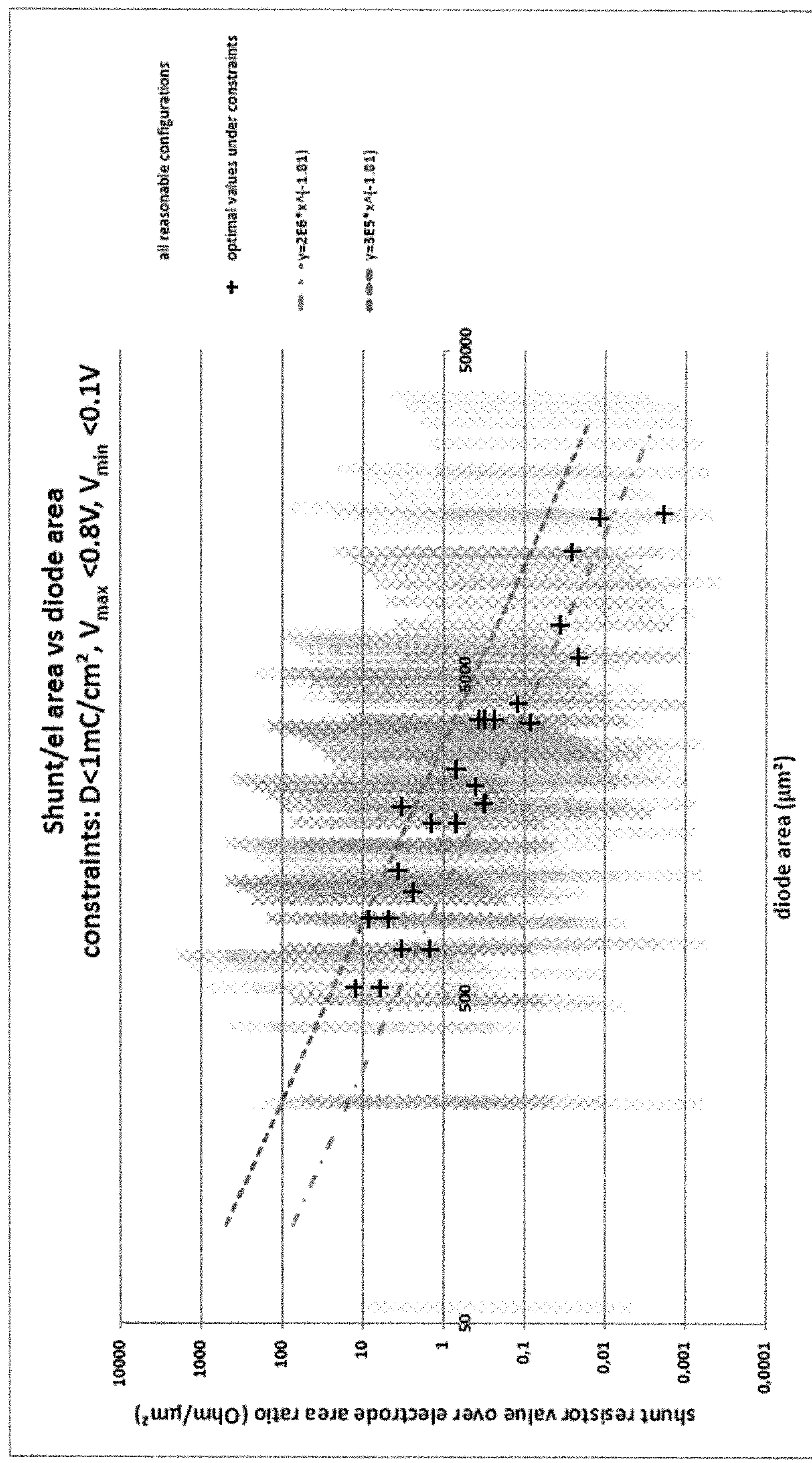
FIGS. 7 to 11 show diagrams for different constraining parameters a and n according to embodiments of the present invention.

FIG. 7 shows a diagram displaying, on a double-logarithmic plot and marked by "x" such parameter configurations for pixels of a pixel array 1, which are, in generally, reasonable and technically possible. In the diagram, the X-axis represents a size (here, an area) of the diode, e.g., the effective diode area. The Y-axis of the diagram shows the corresponding relation of the shunt resistor value divided by the electrode area derived from Equation (2) as defined above. Those parameter coordinates marked by a "+" in FIG. 7 represent sets of parameters, which are constrained according to the inventive considerations of the present invention.

These constraints may for instance require that the electrode is enabled to provide a specific charge at a specific charge density. That charge density may in particular be about 0.35 $mC/cm^2$. An upper limit of the charge density preferably is at 1 $mC/cm^2$. The charge density may be up to 1.5 $mC/cm^2$. Further these constraints may require that a maximum voltage between the electrode 14 and the counter electrode 18 may not be exceeded in response to a stimulation impulse. In particular, the voltage may be intended to be kept below the hydrolysis voltage of water. As one example considered for the exemplified embodiments according to FIGS. 7 to 11, the maximum voltage may be limited to about 0.8 V. A minimal voltage provided by the electrodes on the other hand according to these embodiments for the specific lighting parameters was considered to be less than 0.1 V. Moreover, these constraints may, in some embodiments, require that the resistance of the resistor 16 allows a sufficiently fast charge balancing, preferably corresponding to a residual DC current, reflecting an unbalanced charge over time, of less than 0.1 μA, while maximizing the charge available for the stimulation. Reduction of the residual DC current, thus charge balancing the electrodes, may allow more controlled stimulation of tissue and therefore increase the reliability of the pixel or pixel array.

As indicated, those pixels and pixel arrays displaying such parameter sets may be described by the above Eqn. (2). In the exemplified embodiment of FIG. 7, the exponent n is n=−1.81. The dotted and the line-dotted lines in FIG. 7 represent an upper and a lower limit of the constant a in Eqn. (2), with the constant a being $3 \cdot 10^5$ and $2 \cdot 10^6$, respectively. These lines represent straight lines defined by the Equation (2), when rearranged according to the following Equation (3):

$$R/E_{area}=a \cdot D^n_{area} \quad \text{(Eqn. 3)}$$

That definition applies in the same way for the FIGS. 8 to 11 as discussed below.

Figure 8:
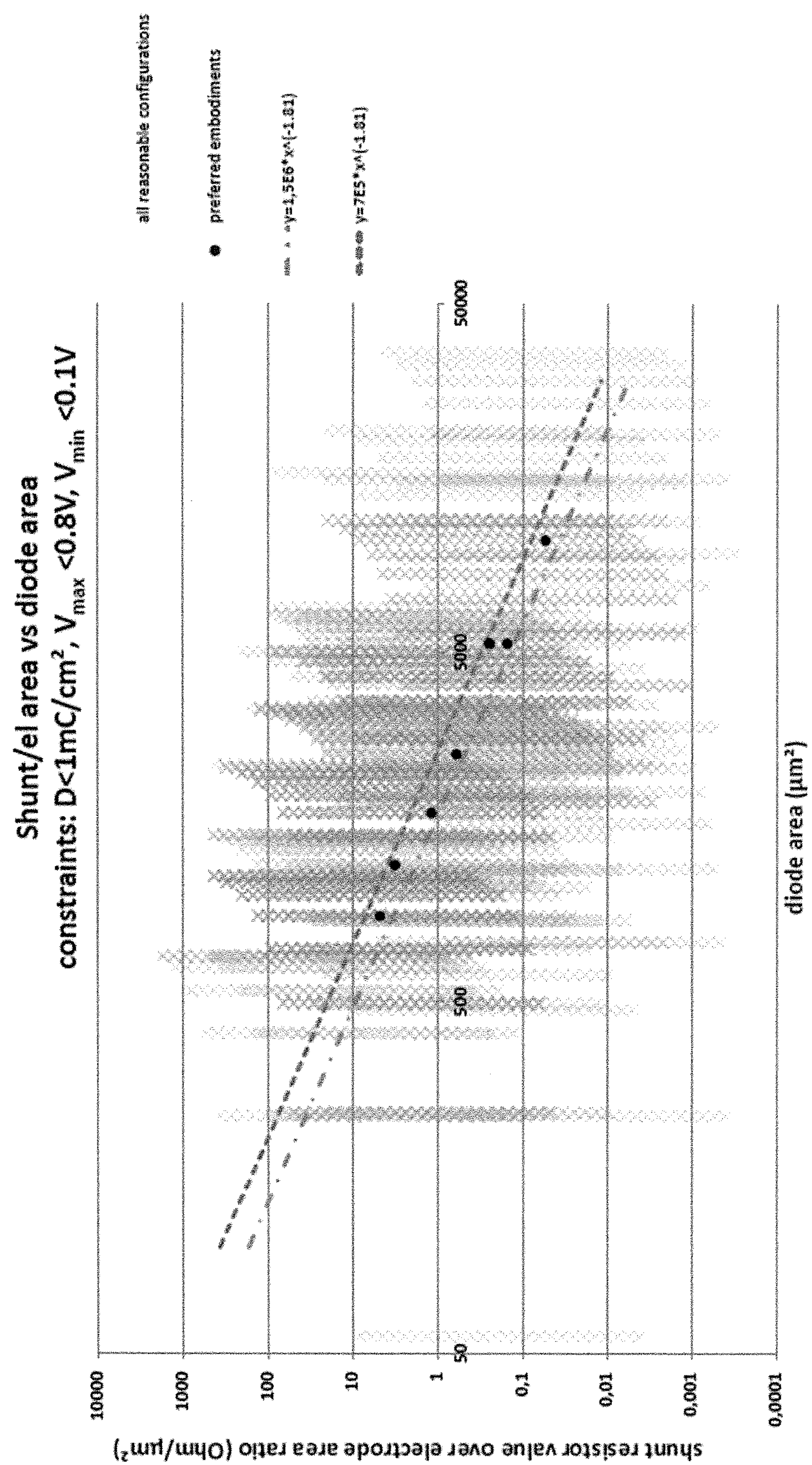

FIG. 8 shows further preferred parameters. These parameter sets are indicated with a black circle (•) in the FIG. 8. As a comparison, FIG. 8 also displays those configurations, which may generally be available as reasonable theoretical configurations. The upper and the lower limits of the embodiments according to FIG. 8 may be defined by $a=7 \cdot 10^5$ and $a=1.5 \cdot 10^6$, respectively.

Figure 9:
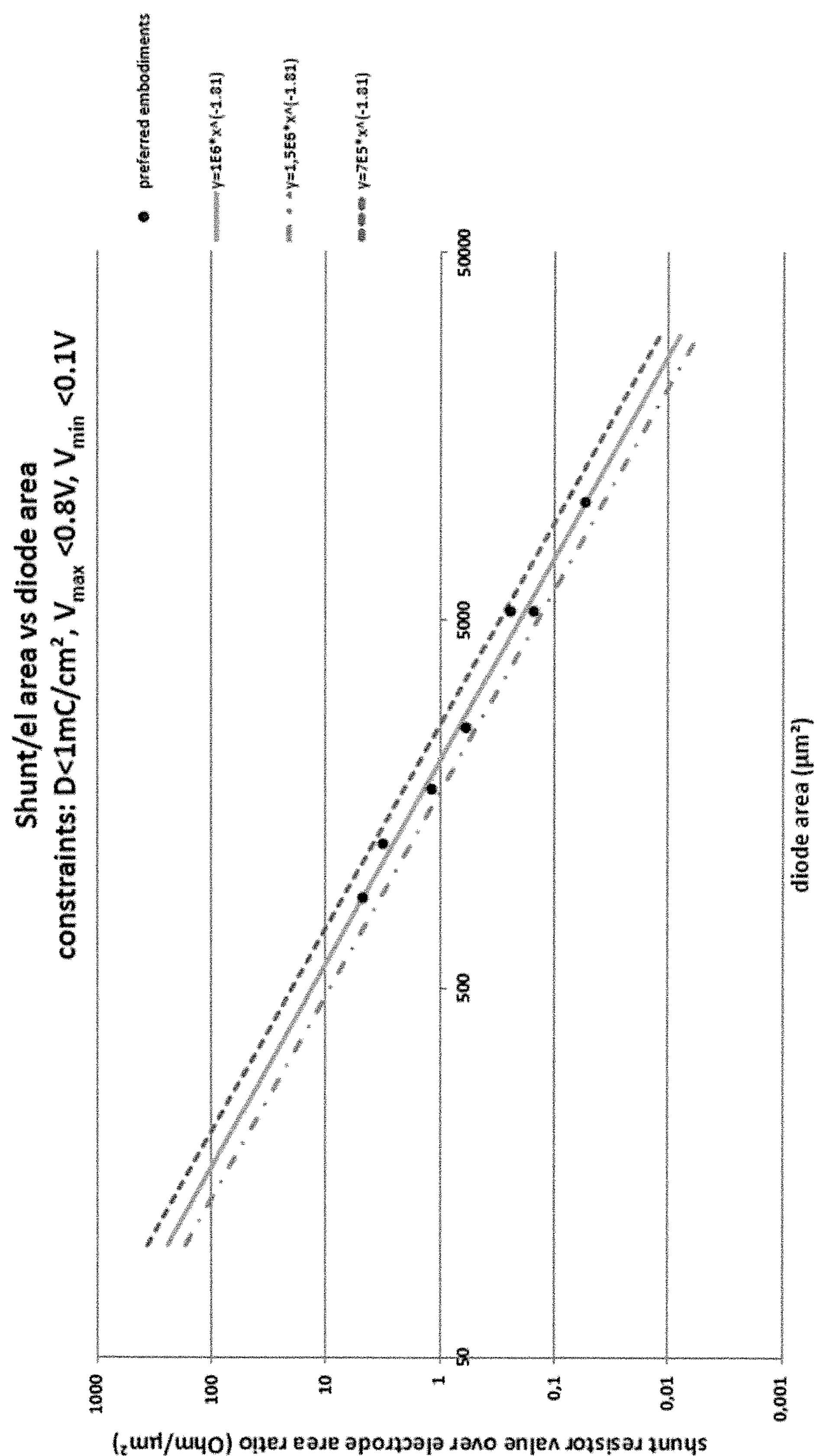

FIG. 9 shows the same diagram as FIG. 8, without displaying all possible parameters sets, and by adding a straight line approximating a preferred center value for the parameter sets of the most preferred embodiments. That line is defined by the constant $a=10^6$ and the exponent n=−1.81. It will be noted that, on the logarithmic plot shown in FIGS. 7 to 11, a common error on the order of 10-50% may be considered as deviation form that preferred central value.

Figure 10:
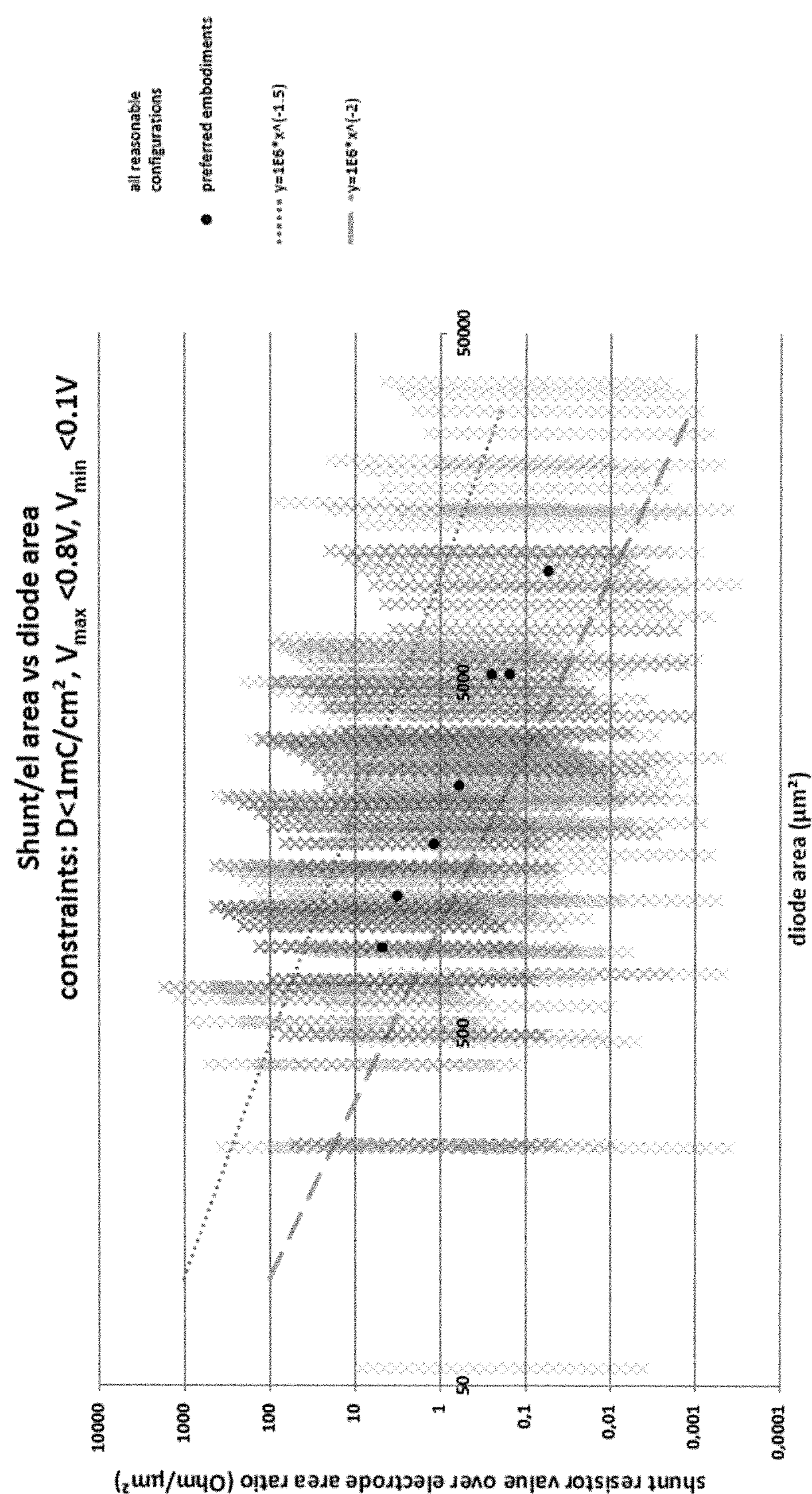

FIG. 10, similarly to FIGS. 7 to 9 shows a diagram of those technical realization, which may theoretically be considered. Further, as in FIGS. 8 and 9, FIG. 10 shows the most preferable embodiments according to the present invention indicated with black circles (•). The lines displayed in FIG. 10, however, indicate an upper and a lower limit of lines defined by above Equation (3), for different exponents n. The exponent for the upper and lower limit of parameter sets in FIG. 10 is defined by n=−1.5 and n=−2, respectively.

Figure 11:
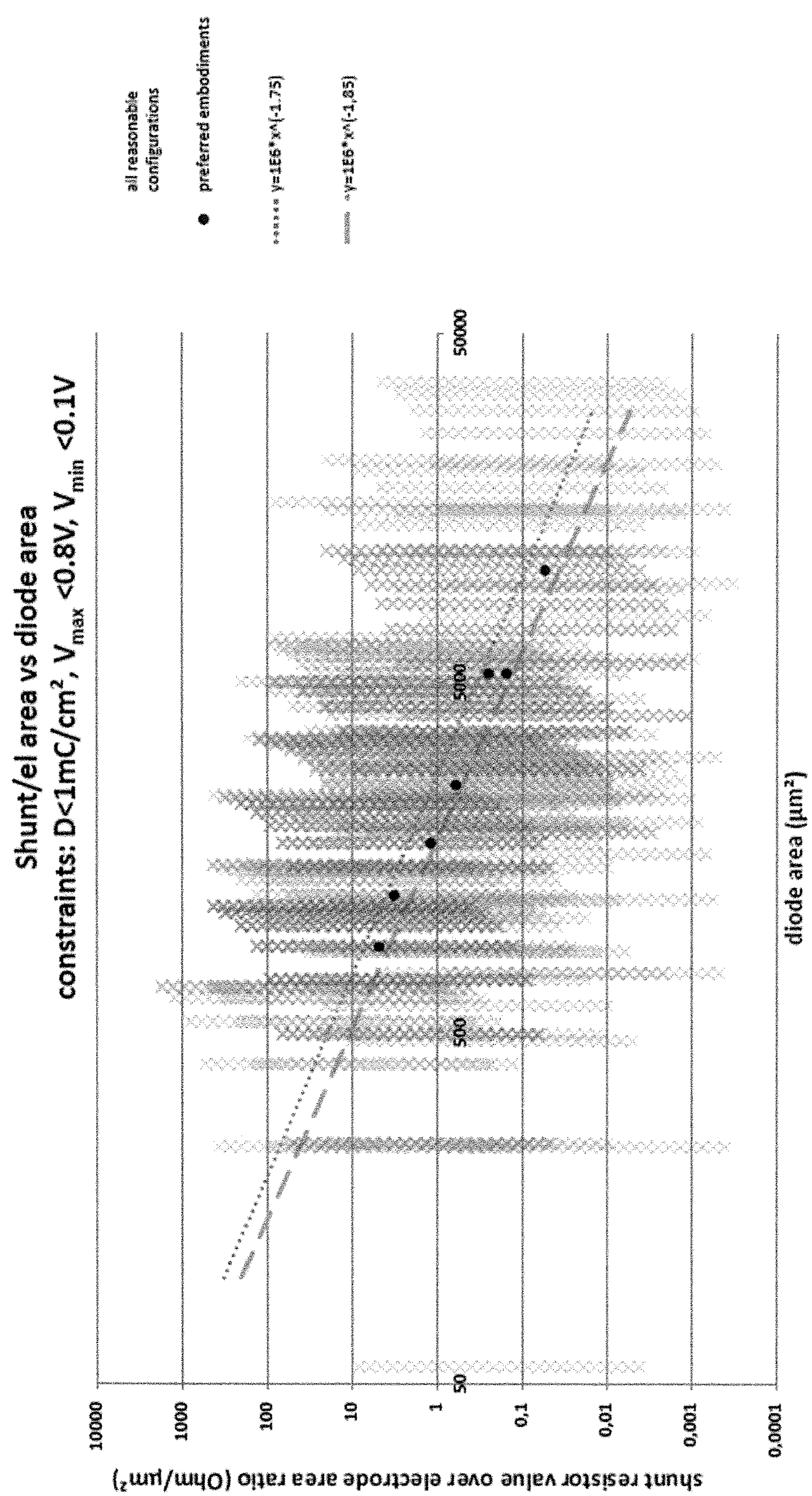
Figure 12:
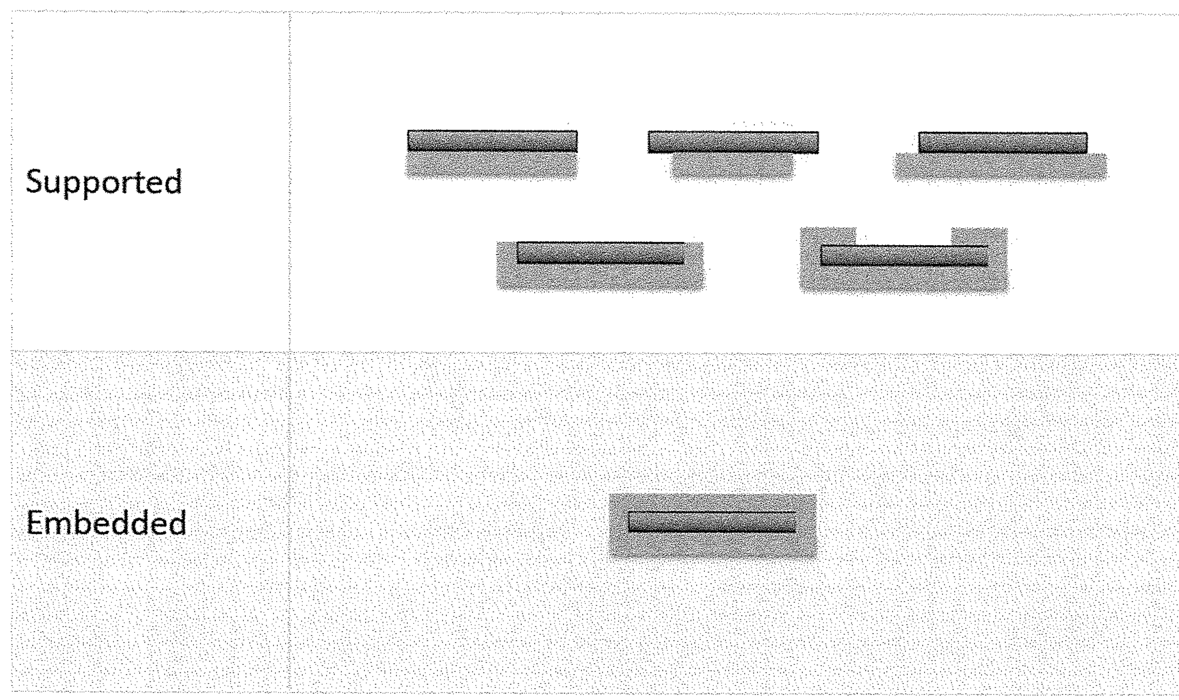
FIG. 12 schematically illustrates different configuration of supported and embedded photosensitive arrays 5 according to the invention. Dark grey rectangles represent electrically stimulating or photosensitive elements 50. Light grey areas represent substrates coating/embedding said elements.
Figure 13:
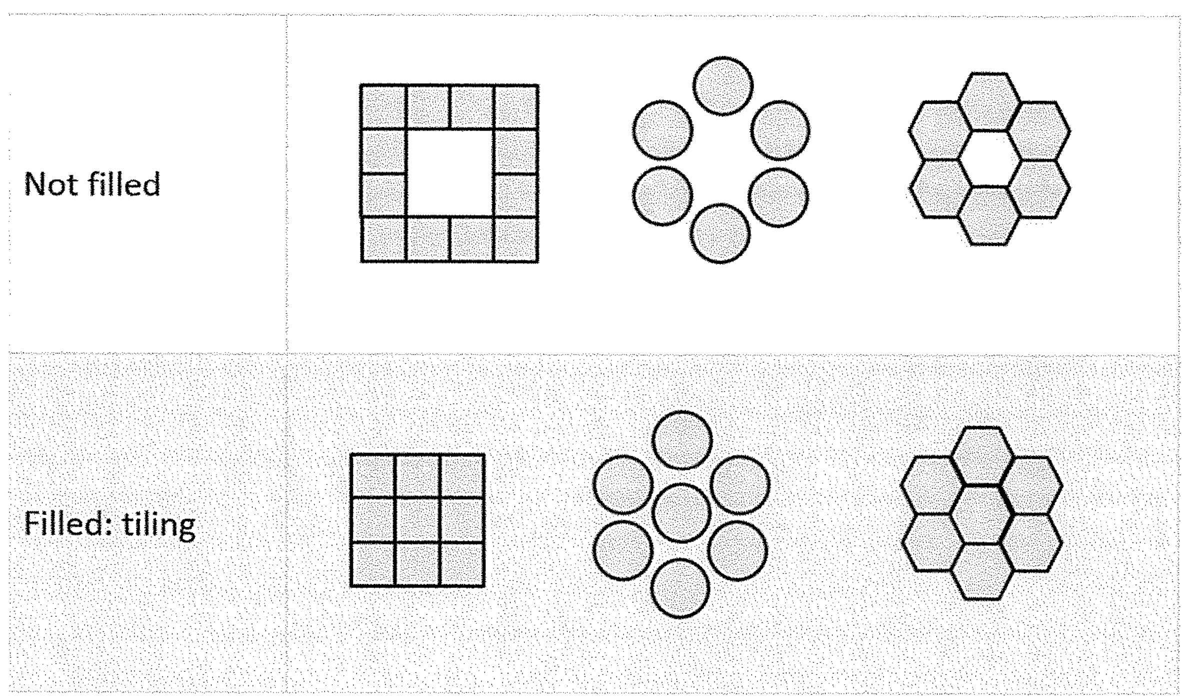
FIG. 13 schematically illustrates different shapes and tiling patterns/arrangements of a plurality of electrically stimulating or photosensitive elements 50 comprised by the supported or embedded photosensitive arrays 5 of the invention. Rectangular (left), round (middle) and hexagonal (right) shapes represent electrically stimulating or photosensitive elements.

Similar to the diagram of FIG. 10, FIG. 11 shows a diagram with limiting lines resulting from different exponents n. An upper limit herein is defined by an exponent of n=−1.75 and a lower limit is defined by an exponent of n=−1.85.

It should be noted that the upper and the lower limit according to the above examples display the boundaries of ranges of possible parameter sets. That is to say that any parameter sets falling between those areas delimited by the lines representing the upper and lower value shall be considered to be part of the idea to provide a pixel or pixel array with enhanced properties.

EXAMPLES

The following examples describe manufacturing methods for various electrically stimulating, on particular photosensitive, arrays according to the invention.

Example 1: Manufacturing of Supported Arrays

Parylene

Photosensitive elements are placed in a row on a plate (for example PTFE plate to avoid adherence of the film on the plate) with electrode side downward on the plate. A Parylene C film of 1 to 10 μm is deposited of on the back of the implants (Thin film deposition). The parylene film is cut to the desired shape.

Polyimide

Option 1: Photosensitive elements are assembled on a polyimide film for example by gluing.

Option 2: Photosensitive elements are integrated in a layer of polyimide on the wafer in the production process of the implants.

Option 3: A film of polyimide is deposited on the back of the photosensitive elements (thin film deposition). Arrays are cut to the desired shape.

Biological Glue

Photosensitive elements are placed in a row in a fixture (for example PTFE fixture to avoid adherence of the film on the plate) with electrode side downward in the fixture. The fixture must comprise a cavity or a few microns depth on top of the implant in the shape of the desired substrate. A film of up to 100 μm of polymer glue is deposited on the back of the photosensitive elements in the cavity. The glue is cured with UV light.

PDMS (Silicone)

A film of up to 100 μM of PDMS is deposited on the back of the photosensitive elements and cured. The array is cut to the desired shape.

Example 2: Manufacturing of Embedded Arrays

Collagen

Photosensitive elements are embedded in non-cross-linked collagen. Subsequently, cross-linking is induced, forming a membrane of collagen around the photosensitive elements.

Hyaluronic Acid

Photosensitive elements are soaked in viscous hyaluronic acid. Hyaluronic acid-embedded photosensitive elements can be delivered below the macula by flushing the drop of hyaluronic acid embedding the photosensitive elements.

The invention claimed is:

1. A photosensitive array comprising:

an array of at least two photosensitive elements, each said photosensitive elements comprising at least one pixel array having at least one diode, a stimulating electrode, a counter electrode, and a resistor, wherein said array comprises at least two photosensitive elements embedded in a biodegradable substrate.

2. The photosensitive array according to claim 1, wherein each photosensitive element comprises a plurality of pixel arrays.

3. The photosensitive array according to claim 1, wherein said photosensitive elements are photosensitive chips.

4. The photosensitive array according to claim 1, wherein a resistance of the resistor is based upon a predetermined relation of resistance, size of the stimulating electrode, and size of the diode.

5. The photosensitive array according to claim 1, wherein the resistance of the resistor is determined by the formula:

$$R=a\cdot(D_{area}{}^{\wedge}n)\cdot E_{area}$$

wherein:

R is a resistance of the resistor;

$E_{area}$ is an electrode area;

$D_{area}$ is an effective diode area;

n is an exponent; and a is a constant.

6. The photosensitive array according to claim 1, comprising an array of two, three or four photosensitive elements.

7. The photosensitive array according to claim 1, wherein said at least two photosensitive elements have a substantially elongated, circular, elliptic, triangular, quadrangular, pentagonal, hexagonal, heptagonal or octagonal shape.

8. The photosensitive array according to claim 1, wherein said array comprises at least two photosensitive elements disposed in or on said substrate at a distance of at least 0.01 mm.

9. The photosensitive array according to claim 1, wherein said at least two photosensitive elements are disposed in or on the substrate substantially linearly, in a serpentine, circularly, triangularly, quadrangularly, pentagonally, hexagonally, heptagonally, octagonally, in regular or non-regular tiling patterns, honeycomb pattern, grid pattern, filled or non-filled patterns, uniform or non- uniform patterns, or arbitrarily/asymmetrically.

10. The photosensitive array according to claim 1, further comprising a coating.

11. The photosensitive array according to claim 10, wherein said coating is contiguous or non-contiguous.

12. The photosensitive array according to claim 10, wherein at least one of the substrate and the coating consists of a material which is (a) sufficiently flexible to adapt to a shape of a part of a body it is implanted into and (b) sufficiently rigid to prevent folding of the photosensitive implant upon and/or after implantation.

13. The photosensitive array according to claim 10, wherein at least one of said substrate and said coating is biocompatible.

14. The photosensitive array according to claim 10, wherein at least one of said substrate and said coating is electrically non-conductive.

15. The photosensitive array according to claim 10, wherein at least one of said substrate and said coating is configured to allow the stimulating electrodes of the photosensitive elements to stimulate surrounding target cells and/or tissues.

16. The photosensitive array according to claim 10, wherein said coating is biodegradable.

17. The photosensitive array according to claim 10 comprising a top layer disposed on the photosensitive elements.

18. The photosensitive array according to claim 10, wherein at least one of said substrate, said coating and a top layer comprises notches or holes.

19. The photosensitive array according to claim 10, wherein at least one of said substrate, said coating and a top layer comprises at least one active agent selected from an anti-infective agent, an anti-inflammatory agent, a gene-therapy agent and a therapeutic cell.

20. The photosensitive array according to claim 10, wherein at least one of an upper and lower surface of said substrate and said coating are colored differently.

21. The photosensitive array according to claim 1, wherein said substrate is configured as a layer supporting the photosensitive elements disposed thereon.

22. The photosensitive array according to claim 21, wherein said substrate is configured as a film or a membrane.

23. The photosensitive array according to claim 21, wherein the photosensitive elements extend beyond at least one of the lateral margins of said substrate.

24. The photosensitive array according to claim 21, wherein said substrate has a length of at least 1 mm, 2 mm, 3 mm, 4 mm, 5 mm, 6 mm, 7 mm, 8 mm, 9 mm or 10 mm, or between 3 mm and 7 mm.

25. The photosensitive array according to claim 21, wherein said substrate has a width of at least 0.1 mm, 0.2 mm, 0.3 mm, 0.4 mm, 0.5 mm, 0.6 mm, 0.7 mm, 0.8 mm, 0.9 mm, 1.0 mm, 1.1 mm, 1.2 mm, 1.3 mm, 1.4 mm or 1.5 mm, or between 0.5 mm to 1 mm.

26. The photosensitive array according to claim 21, wherein said substrate has a thickness of between 1 μm and 500 μm.

27. The photosensitive array according to claim 17, wherein said substrate and/or said top layer comprises material selected from parylene, polyimide, polydimethylsiloxane (PDMS), polyester or a polymer including poly (lactic acid) (PLA), poly(glycolic acid) (PGA), poly(lactid-co-glycolic acid) (PLGA) or a bioadhesive.

28. The photosensitive array according to claim 1, wherein said substrate is configured as a capsule enclosing said photosensitive elements.

29. The photosensitive array according to claim 28, wherein said substrate is a solid, a gel or a viscous fluid.

30. The photosensitive array according to claim 10, wherein said substrate and/or said coating comprises a material selected from collagen, hyaluronic acid, polyethylenglykol (PEG), poly(lactic acid) (PLA), poly(glycolic acid) (PGA), poly(lactid-co-glycolic acid) (PLGA), gelatin, hydrogel, or a bioadhesive.

31. The photosensitive array according to claim 28, wherein said capsule is assembled from at least two different materials.

32. The photosensitive array according to claim 1, comprising a substrate configured as a layer, and/or a substrate configured as a capsule.

33. The photosensitive array according to claim 1 for use as an implant, or a retinal implant.

34. The photosensitive array according to claim 1, wherein said substrate is configured as a film or a membrane.

35. The photosensitive array according to claim 34, wherein said substrate comprises a flexible material, a biocompatible material, an electrically non-conductive material, parylene, polyimide, polydimethylsiloxane (PDMS), polyester a polymer including poly(lactic acid)

(PLA), poly(glycolic acid) (PGA), poly(lactid-co-glycolic acid) (PLGA) or a bioadhesive, or combinations thereof.

36. The photosensitive array according to claim 34, further comprising a coating .

37. The photosensitive array according to claim 36, wherein said coating consists of a biodegradable material, a non-biodegradable material, collagen, hyaluronic acid, polyethylenglycol (PEG), poly(lactic acid) (PLA), poly(glycolic acid) (PGA), poly(lactid-co-glycolic acid) (PLGA), gelatin, a hydrogel adhesive, a biological adhesive, or combinations thereof.

38. The photosensitive array according to claim 1, wherein said array comprises an array of a plurality of two, three, four or more photosensitive elements, each photosensitive element comprising a plurality of pixel arrays , wherein said elements are disposed in a substrate , and wherein said substrate is configured as a capsule.

39. The photosensitive array according to claim 38, wherein said substrate comprises a flexible material, a biocompatible material, an electrically non-conductive material, collagen, hyaluronic acid, polyethylenglycol (PEG), poly(lactic acid) (PLA), poly(glycolic acid) (PGA), poly(lactid-co-glycolic acid) (PLGA), gelatin, a hydrogel adhesive, a biological adhesive, or combinations thereof.

40. A method for producing a photosensitive array according to claim 1, comprising (1) providing a substrate;

(2) providing at least two photosensitive elements; and (3) embedding said photosensitive elements in said substrate.

41. The method of claim 40, further comprising adding at least one of a coating, a top layer, and a therapeutic agent.

* * * * *